United States Patent
Jalde

(10) Patent No.: US 12,396,927 B2
(45) Date of Patent: Aug. 26, 2025

(54) CLASSIFYING OF A POSITION OF A CATHETER IN RELATION TO A DIAPHRAGM

(71) Applicant: Maquet Critical Care AB, Solna (SE)

(72) Inventor: Fredrik Jalde, Sundbyberg (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 18/871,397

(22) PCT Filed: Nov. 29, 2023

(86) PCT No.: PCT/SE2023/051200
§ 371 (c)(1),
(2) Date: Dec. 3, 2024

(87) PCT Pub. No.: WO2025/116794
PCT Pub. Date: Jun. 5, 2025

(65) Prior Publication Data
US 2025/0186307 A1    Jun. 12, 2025

(51) Int. Cl.
*A61J 15/00*    (2006.01)

(52) U.S. Cl.
CPC ....... *A61J 15/0003* (2013.01); *A61J 15/0088* (2015.05)

(58) Field of Classification Search
CPC ........................... A61J 15/0003; A61J 5/0088
USPC ...................... 604/264; 600/424; 128/204.23
See application file for complete search history.

(56) References Cited

U.S. PATENT DOCUMENTS

| | | | | |
|---|---|---|---|---|
| 2007/0276280 A1* | 11/2007 | Blomberg | ............ | A61B 5/7203 600/546 |
| 2009/0137911 A1* | 5/2009 | Sinderby | ............. | A61M 16/024 600/484 |
| 2010/0116274 A1* | 5/2010 | Jalde | ...................... | A61B 5/353 600/509 |
| 2022/0095980 A1 | 3/2022 | Scharf | | |
| 2022/0181024 A1 | 6/2022 | Palti | | |

FOREIGN PATENT DOCUMENTS

EP    979118 B1    6/2003

OTHER PUBLICATIONS

International Search Report and Written Opinion dated Jul. 4, 2024 for PCT Application No. PCT/SE2023/051200.
J. Beck et al.: "Effects of muscle-to-electrode distance on the human diaphragm electromyogram", J Appl Physiology (1985), p. 975-985.
Office Action dated Apr. 14, 2025 for U.S. Appl. No. 18/871,399.

* cited by examiner

*Primary Examiner* — Phillip A Gray
(74) *Attorney, Agent, or Firm* — EIP US LLP

(57) ABSTRACT

The present disclosure relates to position monitoring of medical devices, and more specifically to technologies for enabling the automatic monitoring of a position of a catheter in relation to a diaphragm. Aspects of the disclosure comprises determining training data to be used for training a machine learning algorithm to classify a position of a catheter in relation to a diaphragm of a patient. Further aspects of the disclosure comprising using a trained machine learning algorithm for classifying a position of a catheter in relation to a diaphragm of a patient.

20 Claims, 12 Drawing Sheets

```
┌─────────────────────────────────────────────────────────────────────┐
│  Acquire clinical data comprising a set of bioelectrical signals    │
│  detected by electrode pairs on a catheter                          │
│                                                              S1     │
└─────────────────────────────────────────────────────────────────────┘

┌─────────────────────────────────────────────────────────────────────┐
│  Perform data preparation process on the bioelectrical signals      │
│                                                              S202   │
└─────────────────────────────────────────────────────────────────────┘

┌─────────────────────────────────────────────────────────────────────┐
│  Identify, from the set of bioelectrical signals, a first           │
│  bioelectrical signal associated with an electrode pair positioned  │
│  closest to the diaphragm                                    S203   │
└─────────────────────────────────────────────────────────────────────┘

┌─────────────────────────────────────────────────────────────────────┐
│  Divide the set of bioelectrical signals into at least two subsets  │
│  of bioelectrical signals, wherein each subset comprises signals    │
│  associated with consecutively placed electrodes             S204   │
└─────────────────────────────────────────────────────────────────────┘

┌─────────────────────────────────────────────────────────────────────┐
│  Label each subset of the plurality of subsets according to whether │
│  the associated electrodes are correctly positioned relative to the │
│  diaphragm or incorrectly positioned relative to the diaphragm      │
│                                                              S205   │
└─────────────────────────────────────────────────────────────────────┘

┌─────────────────────────────────────────────────────────────────────┐
│  Store the subsets and their respective labels as training data     │
│                                                              S206   │
└─────────────────────────────────────────────────────────────────────┘

┌─────────────────────────────────────────────────────────────────────┐
│  Use the subsets and their respective labels as training data       │
│                                                              S3     │
└─────────────────────────────────────────────────────────────────────┘
```

Figure 4

```
┌─────────────────────────────────────────────────────────────────────┐
│              Use the subsets and their respective labels as training data │
│                                                                  S3 │
└─────────────────────────────────────────────────────────────────────┘

┌─────────────────────────────────────────────────────────────────────┐
│              Deploy trained machine learning algorithm              │
│                                                                S400 │
└─────────────────────────────────────────────────────────────────────┘

┌─────────────────────────────────────────────────────────────────────┐
│    Receive a catheter data comprising bioelectrical signals detected from the │
│                                  patient                            │
│                                                                S401 │
└─────────────────────────────────────────────────────────────────────┘

┌─────────────────────────────────────────────────────────────────────┐
│      Divide the set of bioelectrical signals into at least two first subsets of │
│    bioelectrical signals, wherein each first subset comprises signals associated │
│                     with consecutively placed electrodes    S403    │
└─────────────────────────────────────────────────────────────────────┘

┌─────────────────────────────────────────────────────────────────────┐
│   Inputting the first subsets of bioelectrical signals into the deployed trained │
│                         machine learning algorithm                  │
│                                                                S405 │
└─────────────────────────────────────────────────────────────────────┘

┌─────────────────────────────────────────────────────────────────────┐
│    Receiving positional information comprising a plurality of input classifications │
│                    from the machine learning algorithm              │
│                                                                S407 │
└─────────────────────────────────────────────────────────────────────┘

┌─────────────────────────────────────────────────────────────────────┐
│   Determine positioning status using positional information output by machine │
│                          learning algorithm                         │
│                                                                  S5 │
└─────────────────────────────────────────────────────────────────────┘
```

Figure 9

CLASSIFYING OF A POSITION OF A CATHETER IN RELATION TO A DIAPHRAGM

CROSS-REFERENCE TO RELATED APPLICATIONS

This application is a 371 National Phase of International Application No. PCT/SE2023/051200, filed Nov. 29, 2023. The above-referenced patent application is incorporated by reference in its entirety.

TECHNICAL FIELD

The present disclosure relates to position monitoring of medical devices, and more specifically to technologies for enabling the automatic monitoring of a position of a catheter in relation to a diaphragm.

BACKGROUND

Catheters are medical devices which allow for the delivery of substances into the body or removal of substances out of the body. In particular, naso/orogastric catheters (also known as nasogastric tubes) allow for the delivery of nutrition, fluids and medications directly to a patient's stomach.

Correctly positioning of such a nasogastric catheter is important to avoid complications such as aspiration of delivered content into the lungs when the catheter is not inserted deeply enough, or physically penetrating a wall of the stomach when the catheter is over-inserted, for example.

Nasogastric catheters may be equipped with sensors to detect bioelectrical signals within the body. The sensors can measure electrocardiographic signals and electromyographic signals emanating from nearby muscles within the body. These signals can aid with assessing whether the nasogastric catheter has been positioned correctly.

Typically, assessing the positioning of a nasogastric catheter is performed by a clinician. The clinician may make a nose-earlobe-xiphoid measurement on the patient to estimate how much of the catheter length should be inserted into the patient. Once the catheter is inserted into the oesophagus, the clinician may monitor the detected electrocardiographic and electromyographic signals in order to determine whether the catheter is positioned correctly, and fine-tune the position if required.

It is especially difficult to accurately assess the positioning of the catheter when no electromyographic signals are detected, which can often be the case when patients are sedated and therefore not breathing spontaneously, often being intubated. Electrocardiographic signals are typically dominant relative to electromyographic signals, such as on the order of 1000 times stronger, which can further complicate detection of the electromyographic signal. In such a scenario where the electromyographic signal is difficult to detect, interpretation of the electrocardiographic signals is required. Inexperienced clinicians may struggle to find and maintain the correct catheter position, however, as electrocardiographic signals are harder to identify visually and frequently lack the precision required for fine-tuning of the catheter placement. Furthermore, in all cases, monitoring of the position is dependent on continued attention by the clinician.

It is desirable to improve methods of assessing catheter positioning.

BRIEF DESCRIPTION OF THE DRAWINGS

FIG. 4 is a flow chart detailing steps performed by the position monitoring system in preparing training data for training a machine learning algorithm;

FIG. 9 is a flow chart detailing steps performed by the position monitoring system in deploying the machine learning algorithm;

DETAILED DESCRIPTION

Figure 1:
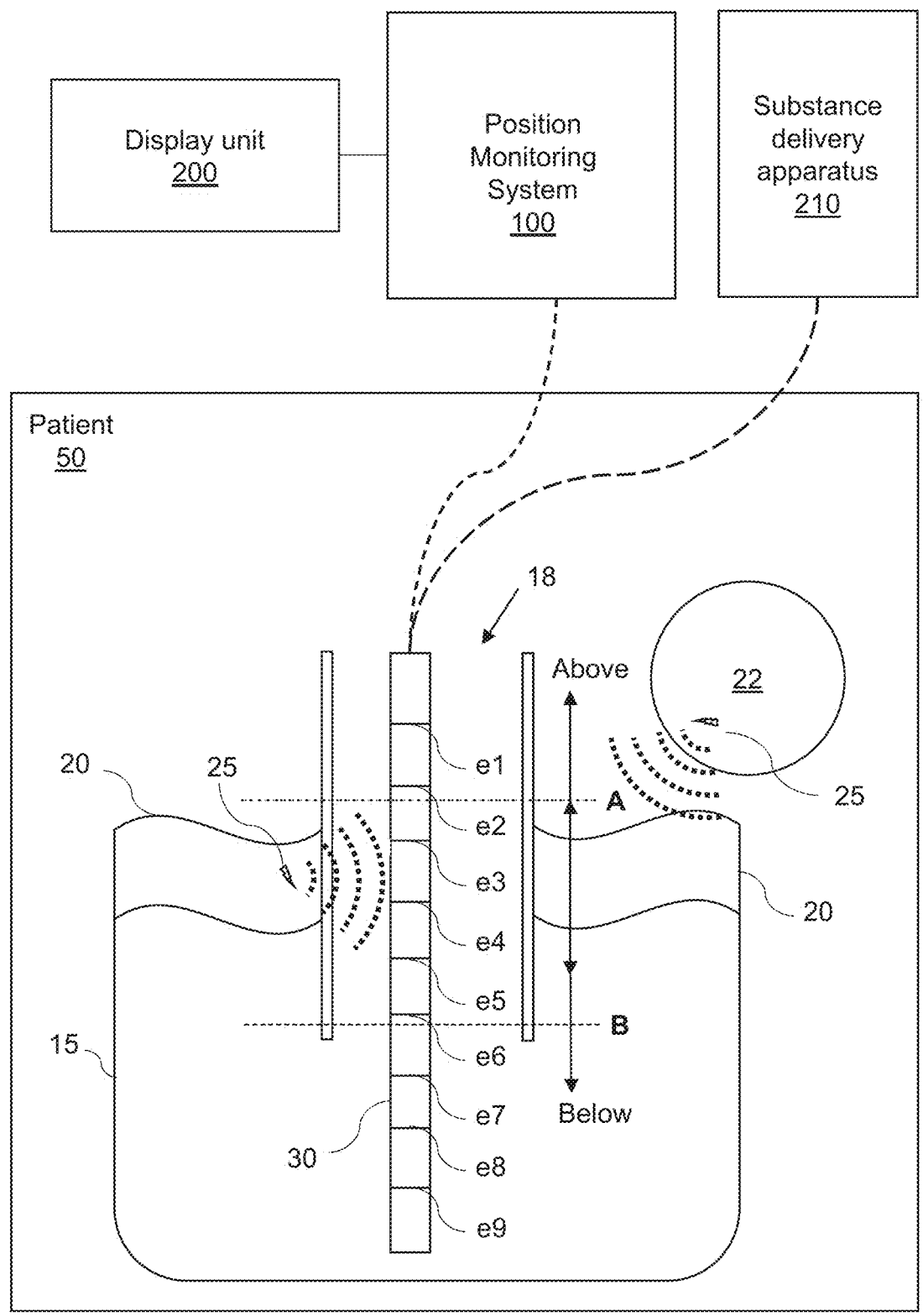
FIG. 1 shows a schematic overview of a position monitoring system for a catheter being used with a patient.

An object of the disclosure is to ascertain correct placement of an oesophageal catheter in a patient. This object is achieved in accordance with the present invention, in some embodiments thereof, by methods and systems for the training and deployment of a machine learning algorithm which can be used in the positioning of a catheter in relation to a diaphragm of a patient. In particular, some embodiments relate to a method and system for determining training data for the machine learning algorithm, and some embodiments relate to a method and system for classifying a position of a catheter in relation to a diaphragm of a patient.

In a first aspect, a method for determining training data to be used for training a machine learning algorithm to classify a position of a catheter in relation to a diaphragm of a patient is provided. The method comprises the steps of: receiving a set of bioelectrical signals detected by a catheter carrying a plurality of electrodes at respective positions along a length of the catheter and thereby causing the electrodes to be located at respectively different distances from a diaphragm of a patient, the plurality of electrodes being divided into a plurality of electrode pairs, each signal being detected by an electrode pair of the plurality of electrode pairs, each signal comprising an electrocardiographic, ECG, component; identifying, from the set of bioelectrical signals, one or more first bioelectrical signals detected by an electrode pair on the catheter determined to be correctly positioned in relation to the diaphragm; dividing the set of bioelectrical signals into at least two subsets of bioelectrical signals, each subset of bioelectrical signals comprising one or more bioelectrical signals and corresponding to a respective group of electrodes associated with the detecting of the one or more bioelectrical signals of the subset of bioelectrical signals, wherein the dividing is performed such that each group of electrodes is a sequence of consecutively placed electrodes along the length of the catheter; labelling each subset of the plurality of subsets, wherein the labelling comprises labelling a subset comprising at least one of the first bioelectrical signals as a subset of signals detected from correctly positioned electrodes; and labelling a subset not comprising any of the first bioelectrical signals as a subset of signals detected from incorrectly positioned electrodes; and including the subsets of bioelectrical signals and their respective labels in the training data.

Typically, available sets of bioelectrical signals are recorded with the catheter in a correct position, thus the data set is unbalanced due to lack of data with wrong position. Moreover, the risk of overfitting is increased for this type of biological data, which tend to be high dimensional and scarce.

The inventors have realized that subsets of signals from a set of bioelectrical signals recorded with the catheter in a correct position may anyway represent a wrongly positioned catheter, since typically, at least some of the signals in the set are recorded from electrodes in the wrong position (i.e., above or below the diaphragm). The method divides the full set of signals into several smaller groups (subsets) of signals. Each subset is classified according to its relative position to the defined "correct position", i.e., relative the first signal(s). A subset comprises one or more bioelectrical signals. Fewer bioelectrical signals in each subset increase the amount of distinct training data. Including more than one bioelectrical signal in a subset advantageously utilize the dependencies in between bioelectrical signals in the training data, by taking into account the information provided by the neighbours of a particular bioelectrical signal, which is resulting from the physical arrangement of the electrodes on the catheter.

Using the techniques described herein, the amount of training data for each possible classification may be increased, while at the same time balancing the training data.

In a second aspect, one or more non-transitory computer-readable media storing instructions executable by one or more processors is provided. The instructions, when executed, cause the one or more processors to perform operations which substantially map to the steps of the method of the first aspect.

In a third aspect, a system is provided. The system comprises one or more processors, and one or more non-transitory computer-readable media storing first computer executable instructions. The non-transitory computer-readable media storing first computer executable instructions, when executed by the one or more processors, cause the system to perform actions which substantially map to the operations caused by the instructions of the second aspect or the steps of the method of the first aspect.

Features of the steps of the method of the first aspect are equally found in the instructions stored by the non-transitory computer-readable media of the second aspect and the actions performed by the system of the third aspect. Embodiments of the method can be understood to correspond to embodiments of the non-transitory computer-readable media and embodiment of the system where appropriate.

In some embodiments, the step of labelling a subset of bioelectrical signals not comprising the first bioelectrical signal as a subset of bioelectrical signals detected from incorrectly positioned electrodes comprises determining whether the electrodes associated with detecting of the one or more bioelectrical signals of the subset are positioned above the diaphragm or below the diaphragm; wherein upon determining that the electrodes are positioned above the diaphragm, labelling the subset of bioelectrical signals as a subset of bioelectrical signals detected from electrodes being above the diaphragm, and upon determining that the electrodes are positioned below the diaphragm, labelling the subset of bioelectrical signals as a subset of bioelectrical signals detected from electrodes being below the diaphragm. This allows the positioning to be more specifically categorised in that a subset with an incorrect position above the diaphragm is distinguished from a subset with an incorrect position below the diaphragm.

In some embodiments, the method further comprising augmenting each bioelectrical signal in a subset, wherein augmenting a bioelectrical signal comprises at least one of: stretch the bioelectrical signal in time, compress the bioelectrical signal in time, or vary the amplitude of the bioelectrical signal. Advantageously, overfitting of the machine learning algorithm may be avoided.

In some embodiments, at least one bioelectrical signal comprises an electromyographic, EMG, component, and the method further comprises applying a filtering algorithm to each bioelectrical signal among the set of bioelectrical signals, wherein the filtering algorithm is configured to at least reduce the respective electromyographic, EMG, component from the respective bioelectrical signal. For example, a stop-band filter could be applied to reduce the EMG component. In other examples, portions of the bioelectrical signal comprising an EMG component are removed and the bioelectrical signal truncated, leaving the remaining bioelectrical signal to be free of or having a reduced EMG component. This can reduce a likelihood that the trained machine learning algorithm becomes overly reliant on detecting an EMG component to accurately classify a position of the catheter, as the EMG component may not be present in patients who are not breathing spontaneously, for example. This allows the trained machine learning algorithm to be deployed in a greater range of clinical scenarios.

In some embodiments, applying the filtering algorithm to a bioelectrical signal comprises identifying a plurality of subparts of the bioelectrical signal, each subpart comprising data detected during a heartbeat of a patient; and calculating an average bioelectrical signal from the plurality of subparts of the bioelectrical signal. Calculating an average can be a straightforward method and relatively computationally inexpensive method of reducing the presence of the EMG component which might only be present in a limited number of the subparts, for example.

In some embodiments, each bioelectrical signal from the set of bioelectrical signals comprises data detected during a plurality of heartbeats of a patient, wherein the method further comprises in each bioelectrical signal from the set of bioelectrical signals, identifying data detected in an intermediate period between two consecutive heartbeats among the plurality of heartbeats; and deleting the identified data from the bioelectrical signal. This can remove data which carries no or limited information from which positioning information can be determined, which may improve the training of the machine learning algorithm.

In some embodiments, the step of identifying, from the set of bioelectrical signals, the one or more first bioelectrical signals detected by an electrode pair on the catheter being the electrode pair among the plurality of electrode pairs positioned closest to the diaphragm comprises in at least one bioelectrical signal from the set of bioelectrical signals, detecting a presence and a size of a electromyographic, EMG, component, and selecting, as the one or more first bioelectrical signals, at least one bioelectrical signals based on the size of the respective EMG component. For example, a largest EMG component is selected, or EMG components above a threshold size are selected. This can provide an accurate method for identifying the closest electrodes and the first bioelectrical signal, for example. Size of the EMG component can be determined using a root-mean-square value (RMS) or peak amplitude, for example.

In some embodiments, the step of labelling a subset not comprising any of the first bioelectrical signals further comprises labelling a subset not comprising any of the first bioelectrical signals with a distance measured between electrodes associated with the subset and the electrodes of the electrode pair associated with a correctly positioned subset of bioelectrical signals. By providing a more granular classification (labelling) of the position of the subset in relation to the first bioelectrical signal, the utility of the output of the machine learning algorithm can be further enhanced, for example, because the clinician can receive an indication of how far from the optimal position the catheter is positioned. This can allow the clinician to more accurately position the catheter.

In some embodiments, the step of labelling a subset not comprising the first bioelectrical signal further comprises labelling a subset not comprising the first bioelectrical signal with a number of intermediate electrodes between an electrode associated with the subset and an electrode of the electrode pair on the catheter being the electrode pair among the plurality of electrode pairs positioned closest to the diaphragm. By providing a more granular classification (labelling) of the position of the subset in relation to the first bioelectrical signal, the machine learning algorithm can indicate the number of electrodes between a given electrode, or a given electrode pair, from the electrode pair positioned most closely to the diaphragm. This can further allow a distance to be inferred from the arrangement of electrodes on the catheter, for example. This can allow the clinician to receive more useful positioning information, and to more accurately position the catheter.

In some embodiments, the dividing of the set of bioelectrical signals is performed such that at least two subsets of bioelectrical signals are partially overlapped such that an electrode associated with detecting of one or more bioelectrical signals of a first subset is also associated with detecting of one or more bioelectrical signals of a second subset. This can generate more subsets of bioelectrical signals from a given set of bioelectrical signals, improving the quantity of training data available. Furthermore, the overlap improves the granularity of the training data as a greater number of electrode positions relative to the diaphragm are considered, which can improve the accuracy of the machine learning algorithm.

In some embodiments, the dividing of the set of bioelectrical signals into at least two subsets of bioelectrical signals is performed such that at each subset is associated with a predefined number of electrodes. This can ensure each subset is equally sized. Each subset being equally sized can reduce bias in the training data set, for example. In examples, each subset is associated with a pair of electrodes. In examples, each subset is associated with pairwise combinations of 3 electrodes, 4 electrodes, or 5 electrodes.

In some embodiments, the dividing of the set of bioelectrical signals into the at least two subsets of bioelectrical signals is performed such that the number of subsets which are determined to be associated with correctly positioned electrodes and are labelled as a subset of signals detected from correctly positioned electrodes is in a predetermined ratio with the number of subsets which are determined to be associated with electrodes positioned above or below the diaphragm and are labelled as a subset of signals detected from electrodes being above the diaphragm or being below the diaphragm. This can allow the training data to comprise a target population ratio of correctly positioned labels with incorrectly positioned labels, that is labels of above the diaphragm or below the diaphragm, which can improve the accuracy of the machine learning algorithm since the training data is balanced according to the requirements of the implementation in which the machine learning algorithm is employed. In embodiments, the predetermined ratio is 1:1. Advantageously, the population of correctly positioned labels is equal to, or substantially similar to, the population of incorrectly positioned labels, providing a fully balanced training data set.

In some embodiments, the bioelectrical signals comprise voltage time series data.

In some embodiments, receiving the set of bioelectrical signals comprises receiving bioelectrical signals from the catheter during use on the patient. Advantageously, the training data may be continuously extended using live data.

In some embodiments, receiving the set of bioelectrical signals comprises receiving pre-recorded bioelectrical signals. That is, the bioelectrical signals may come from historical clinical data.

In some embodiments, the machine learning algorithm is a neural network.

In some embodiments, the plurality of electrodes is equidistantly spaced along the length of the catheter. The machine learning algorithm may be made more accurate because the electrodes are in a regular positional relationship with one another, which increases flexibility in how the set of bioelectrical signals can be divided into subsets. Moreover, equidistantly spaced electrodes may simplify assessing the position of the catheter compared with, for example, an arbitrary distribution of electrodes along a length of the catheter.

In some embodiments, when the first bioelectrical signal is identified as being associated with an electrode which is a distalmost or proximalmost electrode of the plurality of electrodes relative to the length of the catheter, the set of bioelectrical signals is not used as training data. Advantageously, bioelectrical signals derived from catheters which are entirely positioned too low or too high, for example, may be discarded, thereby improving the effectiveness of the training data.

In some embodiments, each electrode pair is a pair of neighbouring electrodes. That is, the electrodes are adjacent in the sequence of electrodes on the catheter, and are nearest neighbours.

In some such embodiments, the one or more first bioelectrical signals comprises a single first bioelectrical signal detected by an electrode pair on the catheter being the electrode pair among the plurality of electrode pairs positioned closest to the diaphragm.

In a fourth aspect, a method for classifying a position of a catheter in relation to a diaphragm of a patient is provided. The method comprises the steps of (a) receiving a first set of bioelectrical signals detected by a catheter carrying a plurality of electrodes at respective positions along a length of the catheter and thereby causing the electrodes to be located at respectively different distances from a diaphragm of a patient, the plurality of electrodes being divided into a plurality of electrode pairs, each signal being detected by an electrode pair of the plurality of electrode pairs, each signal comprising an electrocardiographic, ECG, component; (b) dividing the first set of bioelectrical signals into at least two first subsets of bioelectrical signals, each first subset of bioelectrical signals comprising one or more bioelectrical signals and corresponding to a respective group of electrodes associated with the detecting of the one or more bioelectrical signals of the subset of bioelectrical signals, wherein the dividing is performed such that each group of electrodes is a sequence of consecutively placed electrodes along the length of the catheter; (c) inputting the first subsets of bioelectrical signals into a machine learning algorithm trained to classify each subset into a plurality of classes, the classes comprise one or more classes for incorrectly positioned electrodes and a class for correctly positioned electrodes; (d) receiving a plurality of input classifications from the machine learning algorithm; (e) inputting the plurality of input classifications into a pattern recognition function configured to classify the position of the catheter; and (f) using an output classification from the pattern recognition function to classify the position of the catheter.

The method of the fourth aspect can allow for received bioelectrical signals from the catheter to be processed and an output classification generated to classify the position of the catheter. Such an output classification, in some examples, could be a binary classification such as "correctly placed" or "incorrectly placed", and can allow a clinician to quickly assess whether the catheter requires repositioning, or whether the catheter can remain in its current position. In other examples, more granular output classifications can allow for additional levels of information regarding the positioning of the catheter.

In receiving a plurality of input classification from the machine learning algorithm and inputting the plurality of input classifications into a pattern recognition function to determine an output classification, classifications from multiple instances of received bioelectrical signals can be aggregated to assign a collective classification.

By aggregating individual classifications into a collective classification, a decision-making process can be more transparent and interpretable. Stakeholders can investigate how each instance contributes to the overall classification, which is beneficial for trust and understanding, particularly in domains where explanations are required, such as healthcare. For example, if errors occur, it can be more straightforward to trace back through the aggregation process to identify and correct the source of the error at the instance level, compared with trying to diagnose a monolithic machine learning algorithm.

Additionally, the method benefits from being modular, in that the pattern recognition function can be updated without re-training the entire machine learning algorithm. This can improve up-time of a system employing the method as time spent offline for maintenance or updates can be reduced.

Furthermore, training a model to predict an aggregated class may require a large amount of labelled data at the aggregated level, which can be costly or time-consuming to collect. Aggregation methods can make use of more readily available instance-level data or manual experts, and can reduce a requirement for large amounts of labelled data. Also, if the aggregated class is rare or imbalanced in the data set, machine learning algorithms can struggle as there are insufficient examples for the machine learning algorithm to accurately predict such an edge case scenario. In contrast, an appropriate output classification for a rare or imbalanced aggregated class can be straightforwardly identified and accounted for by the pattern recognition algorithm.

In a fifth aspect, one or more non-transitory computer-readable media storing instructions executable by one or more processors is provided. The instructions, when executed, cause the one or more processors to perform operations which substantially map to the steps of the method of the fourth aspect.

In a sixth aspect, a system is provided. The system comprises one or more processors, and one or more non-transitory computer-readable media storing first computer executable instructions. The non-transitory computer-readable media storing first computer executable instructions, when executed by the one or more processors, cause the system to perform actions which substantially map to the operations caused by the instructions of the fifth aspect or the steps of the method of the fourth aspect.

Features of the steps of the method of the fourth aspect are equally found in the instructions stored by the non-transitory computer-readable media of the fifth aspect and the actions performed by the system of the sixth aspect. Embodiments of the method can be understood to correspond to embodiments of the non-transitory computer-readable media and embodiment of the system where appropriate.

In some embodiments, the pattern recognition function is configured to output an output confidence value in association with the output classification, the output confidence value indicating a probability of correct output classification. The output confidence value can be used by a clinician, in addition to the output classification, to assess what actions to take with the catheter, for example, such as retain the catheter in a current position, or to reposition the catheter.

In some embodiments, the pattern recognition function is configured to output a plurality of output classifications, wherein each output classification is associated with a respective output confidence value. The clinician can thereby receive a most likely output classification, a second most likely classification, and so on. This can improve the range of information provided to the clinician in order to allow their assessment of and decision-making process regarding the catheter position to be more accurate, for example.

In some embodiments, the pattern recognition function is configured to compare the plurality of input classifications with a pre-determined list comprising a plurality of candidate combinations of input classifications, wherein each candidate combination is associated with a respective candidate output classification, and wherein the method further comprises determining an output classification based on the pre-determined list. Having such a predetermined list can allow for straightforward processing, error diagnosis and analysis, and interpretation of the decision-making process effectively performed by the pattern recognition function, for example. Updating the pre-determined list, for example by consultation with a clinical expert, can be a quick way to rectify classification errors which may arise, for example, compared with retraining a machine learning algorithm, for example.

In some embodiments, the method further comprises calculating a respective variance of the input classifications from each candidate combination of input classifications in the pre-determined list, and identifying the candidate combination of input classifications resulting in the smallest variance; wherein the output classification is set to the candidate output classification of the identified candidate combination. Calculating the variance of the input classification from the candidate combinations can be a straightforward process which can clearly be interpreted to understand the origin of an output classification, for example.

In some embodiments, calculating a respective variance of the input classifications from each candidate combination comprises calculating a variance of each input classification from a respective corresponding candidate input classification of the candidate combination of input classifications, and aggregating the calculated variances to determine the respective variance of the input classifications. In this way, an instance-wise comparison of input classifications and candidate combinations can occur which can be straightforwardly summated, for example, to determine the respective variance. This can also be easily interpreted to understand the origin of an output classification, for example.

In some embodiments, the method further comprises calculating an output confidence value of the output classification based on the smallest variance.

In some embodiments, the pre-determined list comprises all possible permutations of input classifications as candidate combinations of input classifications, wherein the method further comprises identifying the candidate combination of input classifications from the list being identical to the input classifications, and wherein the output classification is set to the candidate output classification of the identified candidate combination. The pre-determined list can be considered a look-up table.

In some embodiments, the first set of bioelectrical signals is the first set of a plurality of sets of bioelectrical signals, each set of the plurality of sets corresponding to bioelectrical signals detected at a respective time period; and wherein the method further comprises: performing step (b)-(d) for each set of bioelectrical signals, thus receiving a plurality of input classifications associated with each set of bioelectrical signals from the machine learning algorithm, forming an aggregation of input classifications which comprises the plurality of input classification received for each set of bioelectrical signals; and inputting the aggregation of input classifications to the pattern recognition function and receiving, as an output from the pattern recognition function, the output classification based on the aggregation of input classifications. This can effectively allow for a time-averaged output classification which can be less sensitive to instantaneous, or short-term, changes in classification, for example, which might arise from a set of bioelectrical signals of the plurality having a different set of classifications to the rest of the plurality of bioelectrical signals, for example. This can be a more useful output to the clinician as it can prevent unnecessary changes in the catheter position which might otherwise arise from instantaneous classification changes.

In some embodiments, the pattern recognition function calculates an intermediate output classification for each plurality of input classification of the aggregation of input classifications, and calculates the output classification based on the majority intermediate output classification. This can be a straightforward method of calculating an output classification which is still time-averaged and resistant to instantaneous changes in output classification, but does not necessarily require more complex calculation steps, for example.

In some embodiments, the method further comprises calculating a respective intermediate confidence value for each intermediate output classification, and calculating an overall confidence value for the output classification based on the intermediate confidence values. The overall confidence value can, similar to the aforementioned overall confidence value calculated for a single set of bioelectrical signals, provide the clinician with an indication of how reliable the output classification is, and the probability that it might be wrong, for example.

In some embodiments, the first set of bioelectrical signals is the first set of a plurality of sets of bioelectrical signals, each set of the plurality of sets corresponding to bioelectrical signals detected at respective time period; and wherein the method further comprises performing step b)-d) for each set of bioelectrical signals, thus receiving a plurality of input classifications associated with each set of bioelectrical signals from the machine learning algorithm, forming an aggregation of input classifications which comprises the plurality of input classification received for each set of bioelectrical signals; and calculating a set of averaged input classifications based on the aggregation of input classifications; and inputting the set of averaged classifications to the pattern recognition function and receiving, as an output from the pattern recognition function, the output classification based on the averaged classifications. This can allow a pattern recognition function which is setup for use with a single set of input classifications to be used, for example, by effectively time-averaging or otherwise the aggregation of input classifications into set of averaged input classifications. This can allow the output classification to be less sensitive to instantaneous, or short-term, changes to the input classifications, for example, which can aid the clinician in determining whether the catheter is appropriately placed or not.

In some embodiments, the pattern recognition function is configured to output one from: a first output classification corresponding to the catheter being positioned too low relative to the diaphragm of the patient, a second output classification corresponding to the catheter being positioned correctly relative to the diaphragm of the patient, and a third output classification corresponding to the catheter being positioned too high relative to the diaphragm of the patient. In examples, the pattern recognition function is configured to output a distance from a correct positioning of the catheter, for example. In examples, the pattern recognition function is configured to output a number of electrodes from a correct positioning of the catheter, for example. The pattern recognition function may output one or more of the above output classifications, for example.

The embodiments described above can allow a catheter to be inserted into a patient and a position of the catheter to be continuously and automatically monitored. This can make it easier for a correct position of the catheter to be found and/or maintained. Having the catheter automatically monitored can avoid the need to perform other processes, such as an x-ray, to confirm the position, which are typically time-consuming and expensive. A decreased risk of incorrectly positioning the catheter can reduce the risk of the feeding tube perforating the duodenum, for example, or a reduced risk of aspiration which can otherwise cause pneumonia, for example.

The embodiments also benefit devices operated in tandem with the catheter. For example, in clinical scenarios employing ventilation techniques such as neurally-adjusted ventilatory assistance (NAVA), a reliable, continuous source of bioelectrical signals from the catheter is required. Accurate positioning of the catheter by embodiments allows for this reliable source of bioelectrical signals to be provided to the ventilation system. Furthermore, false triggers caused by signal leakage brought about by incorrect positioning of the catheter can lead to false alarms, inaccurate monitored values of respiratory rate and/or tidal volume, and false triggering of the ventilation system which leads to asynchrony between the patient and the ventilation system. Accurate positioning of the catheter can address these issues.

The present invention will now be described more fully hereinafter with reference to the accompanying drawings, in which embodiments of the invention are shown.

FIG. 1 illustrates schematically an overview of a patient 50 having an oesophageal catheter 30 which extends down their oesophagus 18 into their stomach 15 and records bioelectrical signals 25, such as electrocardiographic, ECG, signals from the heart 22, and electromyographical, EMG, signals from the diaphragm 20.

The catheter 30 comprises a plurality of electrodes, labelled $e_1$ to $e_9$, at respective positions along the length of the catheter 30. In this example, there are nine electrodes, but it will be appreciated that in other examples there may be a different number of electrodes. In the example of FIG. 1, the electrodes $e_{1-9}$ are arranged as a linear array of equidistantly spaced electrodes, such that each electrode is spaced by substantially a same distance from its two neighbours. Each electrode is located at respectively different distances from the diaphragm 20. An electrode can be considered to be above the diaphragm when it is towards the patient's oesophagus, such as when it lies above indicative axis A in FIG. 1. Similarly, the electrode can be considered to be below the diaphragm when it is towards the patient's stomach, such as when it lies below indicative axis B in FIG. 1. That is, above and below should be understood to relate to a degree of insertion of the catheter into the stomach relative to the position of the diaphragm. Similarly, the electrode can be considered to be aligned with the diaphragm, or in the vicinity of the diaphragm, when it lies between indicative axis A and indicative axis B.

Pairs of electrodes, $e_n$ and $e_{x \neq n}$, neighbouring pairs of electrodes, such as $e_n$ and $e_{n-1}$, or $e_n$ and $e_{n+1}$, are used to make the bi-polar measurement and generate the bioelectrical signal. The following discussion considers bioelectrical signals being generated by nearest-neighbour pairs, but more generally non-neighbouring pairs may also or alternatively be used.

Figure 5:
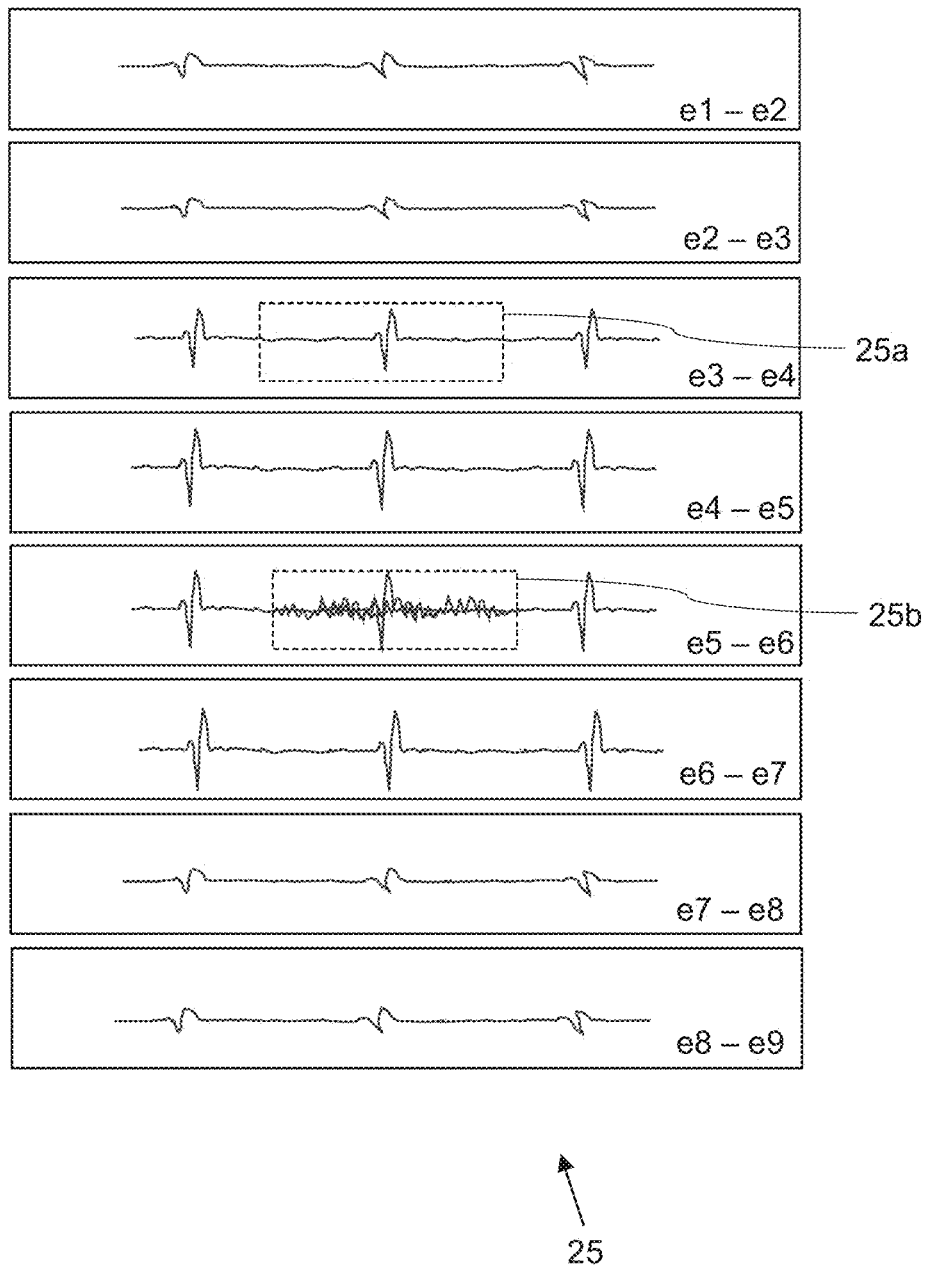
FIG. 5 illustrates an example of bioelectrical signals detected by a catheter.

The nine electrodes thereby produce a set of bioelectrical signals, which in this example is an 8-channel voltage time series data based on the 8 neighbouring pairs. A set of bioelectrical signals can hereafter be understood as a plurality of signals, with each signal of the plurality of signals corresponding to a respective pair of electrodes of the catheter 30. An example of the set of bioelectrical signals detected by the electrodes of the catheter 30 is illustrated by FIG. 5. In the example of FIG. 5, the bioelectrical signals are recorded as voltage time series data at a 2 kHz time resolution and with 20 bits of amplitude resolution. An example of the ECG component of the signal is labelled 25a, and an example of an EMG component is labelled 25b.

The bioelectrical signals 25 typically comprise contributions from both ECG signals and EMG signals. ECG signals are emitted by the heart 22 whenever the patient's heart beats. Given the proximity of the heart 22 to the diaphragm 20, the ECG can be a reliable source of information from which the position of the diaphragm can be inferred. The ECG signal comprises a PQRST complex which describes the pattern of bioelectrical activity of the heart during a cardiac cycle. An initial peak, the P-wave, represents the propagation of a bioelectrical impulse initiated by the sinoatrial node located in the right atrium, traversing both atria of the heart and causing them to contract. The Q, R, S waves collectively delineate the ensuing ventricular contraction triggered by the P wave. The terminal peak, T-wave, represents the recovery of the ventricles, preparing them for the next cardiac cycle. EMG signals are emitted during contraction of the diaphragm, such as during a respiratory effort; that is, when the patient breathes spontaneously, the diaphragm contracts and emits EMG signals.

A position monitoring system 100 receives the signals detected by the electrodes to thereby monitor the position of the catheter 30 within the patient 50. The position monitoring system 100 is described in more detail later in view of FIG. 2. In general, however, the position monitoring system is responsible for determining whether the catheter 30 is correctly positioned or incorrectly positioned, and informing a clinician of the same. In this example, the position monitoring system 100 outputs positioning information which describes whether the catheter 30 is correctly positioned or incorrectly positioned to a display unit 200. The output positioning information and the display of such information is described in more detail later in view of FIG. 13. A substance delivery apparatus 210 administers fluid, nutrients and medication via the catheter 30 to the patient. The substance delivery apparatus 210 may, for example, await correct positioning of the catheter 30 before delivering fluid, nutrients or medication. The correct positioning of the catheter may be confirmed by the position monitoring system 100, and/or by the clinician, for example. It will be appreciated that other components, not illustrated in FIG. 1, may similarly use positioning information from the position monitoring system 100. For example, a ventilation control system may temporarily inhibit ventilation if it is determined that the position of the catheter is incorrect to reduce a risk of falsely triggered breaths which might arise from noise in the received signals due to the incorrect position, for example.

Figure 2:
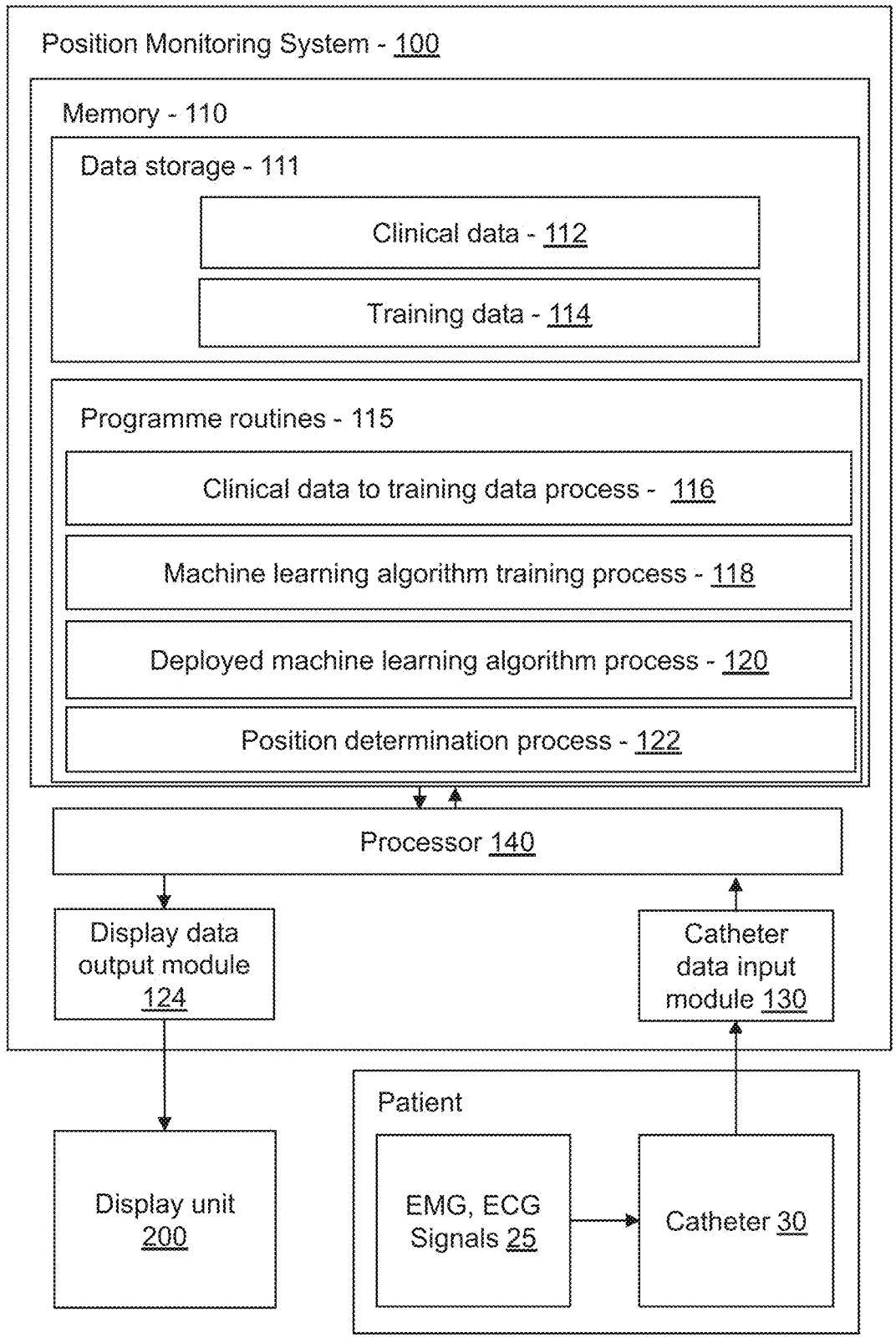
FIG. 2 illustrates schematically a position monitoring system according to examples.

Turning now to FIG. 2, the position monitoring system 100 will be described in more detail. The position monitoring system 100 comprises a processor 140 which interacts with and executes data and programme routines stored in memory 110. In this example, the memory 110 comprises data storage 111 for storing clinical data 112 and training data 114, and stores programme routines 115 which allow for the execution of a clinical data to training data process 116, a machine learning algorithm training process 118, a deployed machine learning algorithm process 120, and a position determination process 122.

As an overview, the position monitoring system 100 receives clinical data 112 which comprises bioelectrical signals detected by catheters, processes the clinical data 112 to create training data 114 for training a machine learning algorithm, trains the machine learning algorithm on the training data 114, and deploys the machine learning algorithm 120. Once deployed, the trained machine learning algorithm 120 can be used to monitor the position of the catheter 30 whilst inserted into a patient 50 based on the bioelectrical signals 25 detected by the catheter 30. This overview is depicted by a flowchart in FIG. 3, in view of which the data 112, 114 and processes 116, 118, 120, 122 are described in more detail, later.

More generally, the position monitoring system 100 can comprise any suitable arrangement or configuration of a computing device or computing devices which permits the storage of clinical data 112 and training data 114, and execution of the clinical data to training data process 116, the machine learning algorithm training process 118, the deployed machine learning algorithm process 120, and the position determination process 122. For example, the storage may comprise remotely accessible cloud storage or locally accessible solid-state disk storage or hard drive storage, or storage on a locally networked server, for example. Programs of instructions for the aforementioned processes may also be stored on the same storage, or in their own respective storage, for example. Similarly, execution of the aforementioned processes may take place on a local processor, such as a local processor of a personal computer located in the clinical environment, or may be executed on a locally networked server, or may be executed on a cloud-based server, for example. Each process may be executed on a respective different processor, or may be performed on a same processor. The position monitoring system 100 may comprise circuitry which is configured to implement (using one or more non-transitory computer-readable media) the functionality described herein. Suitable processors for the execution of a program of instructions include, by way of example, both general and special purpose microprocessors, and the sole processor or one of multiple processors or cores, of any kind of computer. The processors can be supplemented by, or incorporated in, ASICs (application-specific integrated circuits). Those skilled in the art will understand that the above-described exemplary embodiments may be implemented in any suitable software, hardware, or firmware configuration or combination thereof. An exemplary hardware platform for implementing the exemplary embodiments may include, for example, an Intel x86 based platform with compatible operating system, a Windows OS, a Mac platform and MAC OS, a mobile device having an operating system such as iOS, Android, etc. In a further example, the exemplary embodiments of the described methods may be embodied as a program containing lines of code stored on a non-transitory computer readable storage medium that, when compiled, may be executed on a processor or microprocessor.

The position monitoring system 100 of FIG. 2 comprises a catheter data input module 130. The catheter data input 130 receives bioelectrical signal data from the catheter 30 which has detected EMG and/or ECG signals 25 of the patient 50. The catheter data input 130 may be arranged such that the catheter 30 interfaces with a personal computing device of the position monitoring system 100, for example, and a program run on the personal computing device of the position monitoring system 100 processes the data received from the catheter 30. In other examples, an intermediate peripheral device receives the data from the catheter 30, such as an oscilloscope, and an on-board processor such as a field-programmable gate array (FPGA) may perform processing on the received data. The catheter data input 130 may perform data normalization or data cleaning on data received from the catheter, for example. The catheter data input 130 may subsequently provide received data to the processor 140 for storage, for example as clinical data 112, or to be used by a process of the position monitoring system 100. The ways in which the data received by the catheter 30 can be used will be described in more detail later.

The position monitoring system 100 of FIG. 2 comprises a display data output module 124. The function of the display data output module 124 is described in more detail later, but generally receives information for output to the display unit 200. The display data output module 124 may therefore include graphics processing capabilities which can, for example, render graphics related to outputs from the processes of the position monitoring system such as the position determination process 122. Information output by the display data output module 124 and the display unit 200 can be used by the clinician.

Figure 3:
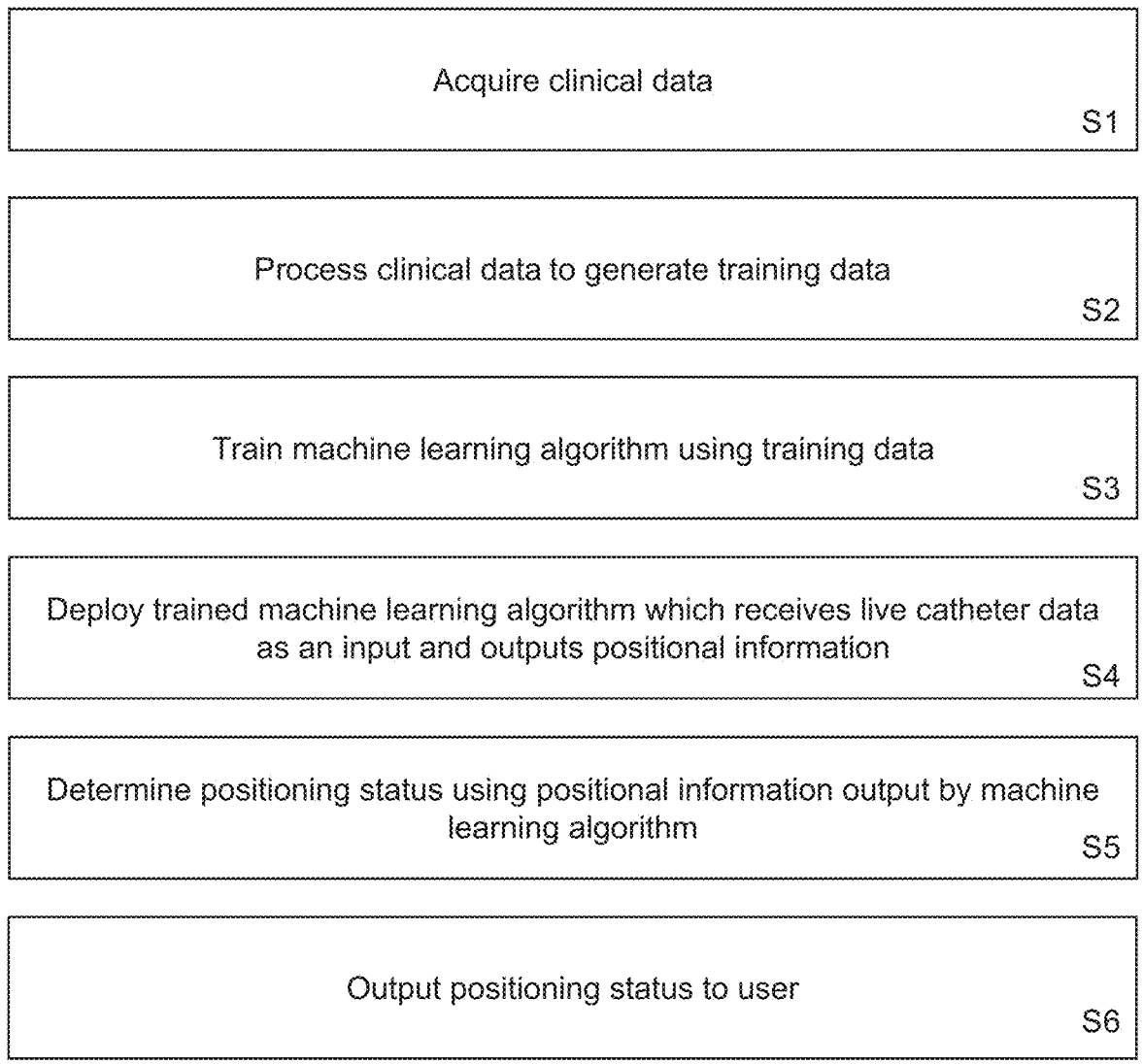
FIG. 3 is a flow chart detailing steps performed by the position monitoring system.

An example of the overarching process flow performed by the position monitoring system 100, will now be described. Steps S1-S6 of the overarching process flow are illustrated in FIG. 3.

At item S1, clinical data 112 is acquired, the clinical data 112 comprising a set of bioelectrical signals detected by electrodes of a catheter, such as the catheter 30 described in FIG. 1.

Generally, the purpose of item S1 is to acquire data which can be used to train a machine learning algorithm, the purpose of which is described below. The clinical data 112 can be data which has been collected recently from a patient, or historical data previously collected. In some embodiments, data is collected from an exclusively adult population and thereby defines adults as a target population for use of the machine learning algorithm. In other embodiments, data may be collected from exclusively paediatric populations, for example, to thereby define children as a target population for use of the machine learning algorithm. In further embodiments, the clinical data comprises a mixture of adult and children, such that a single model can be trained and applied independent of patient age. In yet further embodiments, data recorded from use in animals may be used, either as training data for use on human patients, or for training and use on a veterinary target population, for example. In further embodiments, clinical data 112 is collected during use of the catheter 30. Clinical data collected during use can be added to the set of existing historical clinical data 112, for example, or can be used to form a new set of clinical data 112 based on particular training needs, for example. Clinical data may be acquired from a federated computing system, for example, wherein data is shared between nodes of a network, the data being shared in a standardised, or harmonised, manner which preserves patient privacy.

At item S2, clinical data is processed to generate training data, corresponding to the clinical data to training data process 116 illustrated in FIG. 2. Both clinical data and training data comprise a set of bioelectrical signals detected by electrodes of catheter. As used herein, clinical data refers to the bioelectrical signals prior to being processed to form training data. It is an observation of the inventors that clinical data sets 112 acquired at item S1, such as historical data sets from intensive care units, are typically recorded with the catheter in a correctly placed position. The clinical data sets may be, therefore, from a machine learning perspective, unbalanced, in that there is a lack of data recorded with the catheter in an incorrectly placed position. Generally speaking, the purpose of item S2 is to improve the training data available to the machine learning algorithm trained at item S3. Steps undertaken at item S2 to achieve this are illustrated in FIG. 4 and described in more detail in view thereof, later.

At item S3, a machine learning algorithm is trained using the training data, corresponding with the machine learning algorithm training process 118 depicted in FIG. 2. Generally, the purpose of item S3 is to train a machine learning algorithm such that, given bioelectrical signals detected by the electrodes of the catheter 30, the machine learning algorithm can determine, or classify, whether the catheter is incorrectly placed or correctly placed relative to the diaphragm. The output of item S3 is a trained machine learning algorithm.

At item S4, the trained machine learning algorithm is deployed, corresponding to the deployed machine learning algorithm process 120 depicted in FIG. 2. Generally, the purpose of item S4 is that bioelectrical signals detected by the electrodes of the catheter 30 and received by the position monitoring system 100 at the catheter data input module 130 are used as an input to the trained machine learning algorithm, and positional information is output by the machine learning algorithm.

Figure 10:
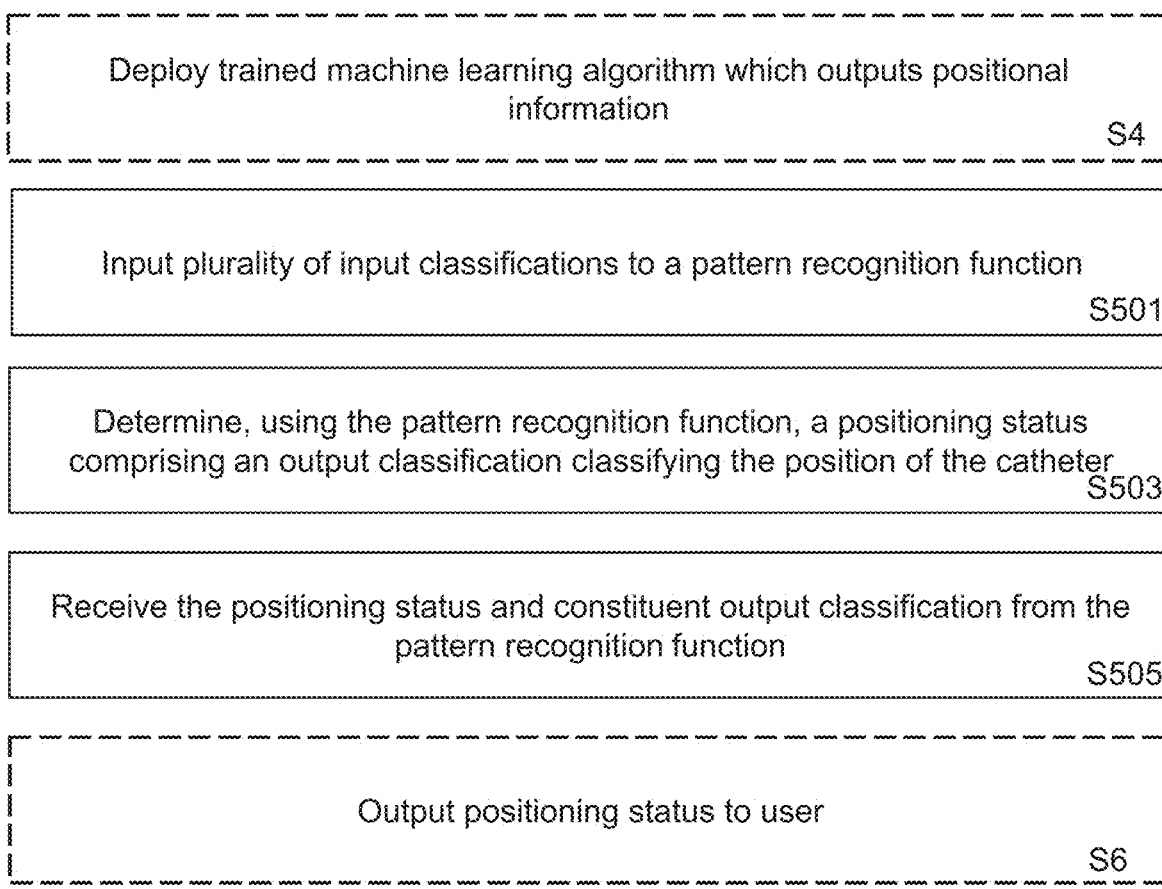
FIG. 10 is a flow chart detailing steps performed by the position monitoring system in determining a positioning status of the catheter being used with a patient.

At item S5, positional information output by the machine learning algorithm is used to determine a positioning status of the catheter, corresponding to the position determination process 122 depicted in FIG. 2. Generally, the purpose of item S5 is to determine how the output by the machine learning algorithm should be utilised to determine a positioning status. Steps undertaken at item S5 are illustrated in FIG. 10 and described in more detail in view thereof, later.

At item S6, the positioning status is output to the user. Generally, the purpose of item S6 is to output the positioning status to the clinician, and corresponds to processes performed by the processor 140 in conjunction with the display data output module 140 and display unit 200 of FIG. 2. For example, the positioning status may indicate the catheter is placed correctly, or incorrectly. In other examples, the positioning status may indicate the catheter is placed incorrectly because it is too high, or incorrectly because it is too low. In further examples, the positioning status may indicate that the catheter is placed incorrectly, and indicate an estimated distance away from being correctly positioned, for example.

The steps S1-S6 do not need to be performed in a strictly sequential manner. For example, steps S1 and S2 may occur multiple times prior to step S3 being performed. For example, steps S1, S2, and S3 may occur multiple times prior to step S4 being performed. The steps S1-S6 do need to be performed in a continuous manner. For example, a first step, such as step S1, may occur at first time, and second step, such as step S2, may occur at a second, significantly later time, such as hours, weeks, or months later, for example.

Processing Clinical Data

The process of processing clinical data to prepare training data will now be described, corresponding to item S3 in FIG. 2. FIG. 4 illustrates a flowchart detailing steps undertaken to process clinical data and prepare training data therefrom. Items S1 and S3 are included in the flowchart to help illustrate the preceding and subsequent processes to item S2.

At item S1, as described previously, clinical data comprising a set of bioelectrical signals detected by electrode pairs on a catheter is acquired. As described previously, the inventors have recognised that such data typically overrepresents correct placement of catheters, and underrepresents incorrect placement of catheters. Steps of item S2, described hereafter, can help address this issue.

At item S202, a data preparation process is performed on the bioelectrical signals. In general, this may comprise some form of data normalisation and/or data cleaning, for example, to ensure a degree of uniformity in the format of bioelectrical signals under consideration, or to optimise the data for use as training data, for example by decreasing a size of the data, or by removing parts of the data which contribute relatively less to the training process.

In examples of this process, the bioelectrical signals are segmented into individual heartbeats. This can be performed based on, for example, identification of the PQRST complex, or a constituent component of the PQRST complex. For example, the R-wave may be detected and used to identify a particular heartbeat. A bioelectrical signal can therefore contain the bioelectrical activity pertaining to one heartbeat detected by an electrode pair. In other examples, a bioelectrical signal comprises a plurality of heartbeats, and segmentation either does not occur, or does not segment down to individual heartbeats.

In examples of this process, data from a temporal window around the R-wave is retained, for example in a window of ±300 ms, whereas data detected in an intermediate period between two consecutive heartbeats among the plurality of heartbeats is deleted. This can ensure the entire PQRST complex within the ECG signal is captured, whilst removing the signal between the heartbeats which contain comparatively little, if any, data of use related to position of the electrode. This can occur in conjunction with segmentation, such that individual heartbeats are isolated, and extraneous data outside of the PQRST complex is deleted, or without segmentation, such that a plurality of heartbeats are recorded, but extraneous data between the PQRST complexes is deleted.

In another example of this process 202, a filtering algorithm is applied to reduce the presence of EMG components within the bioelectrical signals. The filtering algorithm may comprise calculating a moving average of a number of heartbeats, wherein the EMG component is only present on a subset of that number of heartbeats. The moving average thereby reduces an influence of the EMG component. Other filtering algorithms for reducing the EMG component are possible, for example applying a band-stop filter in the EMG frequency spectra (frequencies around 60-100 Hz), or such as entirely excluding heartbeats in which EMG components are detected. Removing the EMG components can ensure the machine learning algorithm learns how to predict catheter positioning based on only ECG components, rather than building a reliance on EMG components. Consequently, the machine learning algorithm may correctly determine the position of a catheter inserted into a patient being sedated and therefore not breathing spontaneously, often being intubated.

In yet another example of this process 202, data augmentation is applied to at least some of the bioelectrical signals. For example, augmenting a bioelectrical signal comprises at least one of: stretch the bioelectrical signal in time, compress the bioelectrical signal in time, or vary the amplitude of the bioelectrical signal. Advantageously, the number of samples by data augmentation may be synthetically increased. Synthetic data augmentation may be important for machine learning classification, particularly for biological data, which tend to be high dimensional and scarce. Data augmentation may also be useful in order to avoid overfitting and to make the machine learning algorithm more robust.

At item S203, a first bioelectrical signal associated with an electrode pair positioned correctly relatively to the diaphragm is identified from the set of bioelectrical signals. As used herein, "first", in the context of first bioelectrical signal, is used as a label, and does not imply any sort of positional information about the bioelectrical signal. Generally, a plurality of first bioelectrical signals may be identified, each of which are associated with a respective electrode pair which are deemed to be correctly positioned relative to the diaphragm. For example, the closest electrode pair to the diaphragm may be identified, but other pairs may be deemed to be positioned closely enough to the diaphragm that they too represent correctly positioned electrodes. The following discussion considers a single first bioelectrical signal for explanatory clarity.

In examples, identifying a first bioelectrical signal may be performed by detecting the presence of EMG components within the bioelectrical signals. By way of an explanatory example, EMG components may be detected within the bioelectrical signals of channels 2-4, but not within channels 1, 5, 7, or 8. The size of the detected EMG components are compared, and the largest EMG component is identified. For example, by way of an explanatory example, channel 5 has the largest EMG component. The size of the EMG component can be an amplitude measurement, such as a peak-to-peak measurement or a root-mean-square amplitude, for example. The associated channel is identified as being detected from the electrode pair positioned most closely to the diaphragm. When channel 5 is identified as having the largest EMG component, electrodes e5 and e6 are identified as being the closest pair of electrodes to the diaphragm. In examples, this approach is extended to identify multiple first bioelectrical signals. For example, bioelectrical signals with EMG components above a threshold size may be considered to be detected by correctly placed electrodes. The threshold size may be relative to an absolute measurement of the EMG component, for example, or may be relative to the size of EMG components of other bioelectrical signals. For example, EMG components within 10% of a maximum detected EMG component may be considered to relate to correctly positioned electrodes. The threshold size may be determined by the precise arrangement of the plurality of electrodes on the catheter or the characteristics of the electrodes. In other examples, the identification process of the one or more first bioelectrical signals may include checking which of the received bioelectrical signals that is associated with a label or flag identifying it as a bioelectrical signal detected by an electrode pair on the catheter determined to be correctly positioned in relation to the diaphragm.

This identification process using the EMG component take place prior to the aforementioned filtering algorithm of item S201, for example, such that the first bioelectrical signal is identified, and then the EMG component subsequently removed. In some examples, a further filtering process can be implemented to the bioelectrical signals to improve the visibility of the EMG component for the purpose of identifying the first bioelectrical signal(s). For example, a band-pass filter can be applied at the EMG component characteristic frequencies and a band-stop filter can be applied at the ECG component characteristic frequencies to thereby reduce the ECG component and relatively enhance the EMG component.

In an alternative embodiment, one of the bioelectrical signals in the set of bioelectrical signals may be labelled (e.g., in the historical clinical data) as being the signal detected by the electrode pair positioned closest to the diaphragm. In this embodiment, no further analysis may be needed to determine the first bioelectrical signal, other than identifying which of the bioelectrical signal comprising this label in the historical clinical data.

At item S204, the set of bioelectrical signals is divided into at least two subsets of bioelectrical signals, wherein each subset comprises signals associated with consecutively placed electrodes. For example, channels 1-3, corresponding to electrode pairs e1 and e2, e2 and e3, and e3 and e4, respectively, can form a subset comprising signals associated with consecutively placed electrodes. Similarly, channels 2-4, 3-5, 4-6, 5-7, and 6-8 may be grouped together. Subsets may, accordingly, overlap, such that a channel is represented in multiple subsets. Allowing for overlap can increase the number of subsets derivable from the set of bioelectrical signals. This can improve the number of electrode positions which are represented by each subset, which can allow for a more accurate estimation of the catheter's position by the trained machine learning algorithm, since dependencies between neighbouring (e.g., channel 2 is neighbouring with channel 1 and 3) bioelectrical signals may be learned and utilized by the machine learning algorithm. Where the subsets comprise signals from multiple channels, the classification problem is effectively converted into a multi-channel time series classification problem. The above discussed data augmentation process may typically be applied on each bioelectrical signal in a subset.

In examples where non-neighbouring pairs of electrodes are used to detect bioelectrical signals, such as e1 and e3, e2 and e4, e3 and e5, and so on, a subset of signals associated with a group of consecutively placed electrodes can nevertheless be prepared when dividing the set of bioelectrical signals. For example, a subset can comprise a bioelectrical signal detected by the pair of e1 and e3, and a bioelectrical signal detected from the pair of e2 and e4. The group of electrodes associated with this subset are therefore e1, e2, e3, and e4, which is a sequence of consecutively placed electrodes along the length of the catheter. A second subset could comprise a bioelectrical signal detected from pair e5 and e7, and a bioelectrical signal detected from pair e6 and e8. The group of electrodes associated with this second subset are therefore e5, e6, e7, and e8, which is also a sequence of consecutively placed electrodes along the length of the catheter. In both cases of detecting bioelectrical signals using neighbouring electrode pairs or non-neighbouring electrode pairs, the subsets may overlap with one another such that an electrode, or electrode pair, is found in multiple subsets.

At item S205, each subset of the plurality of subsets is labelled according to whether the associated electrodes are correctly positioned relative to the diaphragm or incorrectly positioned relative to the diaphragm.

Figure 6:
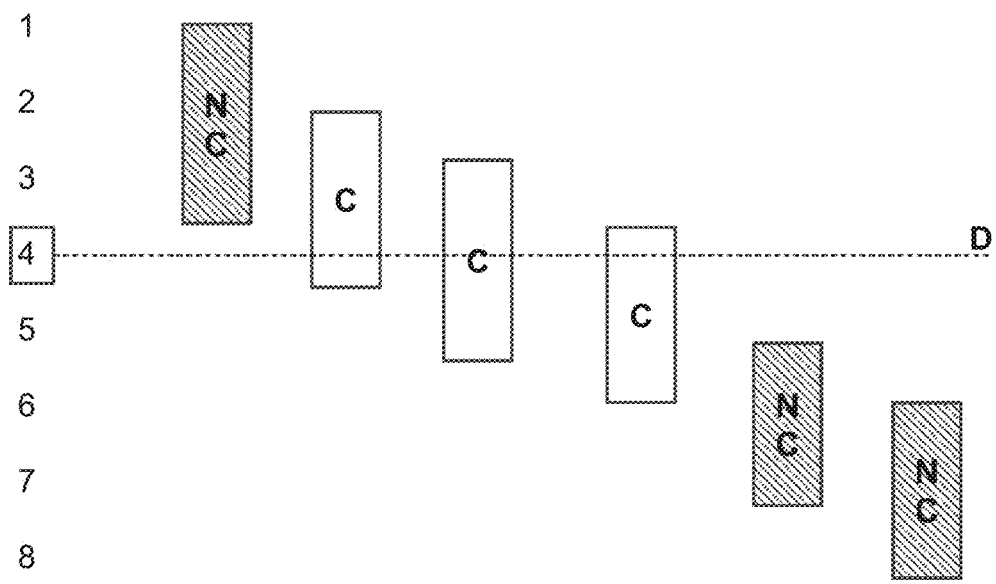
FIGS. 6 and 7 illustrate an example of labelling training data.

In one example of the labelling process, a subset comprising the first bioelectrical signal is labelled as being detected from correctly positioned electrodes. That is, the closest electrodes to the diaphragm are considered to be correctly positioned. Subsets which do not comprise the first bioelectrical signal are labelled as being detected from incorrectly positioned electrodes. This can provide a straightforward method of labelling all the training data, as only identification of the closest electrode pair is required. FIG. 6 illustrates this schematically. In the example of FIG. 6, the diaphragm is closest to electrodes e4 and e5, which correspond with channel 4. Channel 4 is therefore identified as the first bioelectrical signal based on, for example, having the largest EGM component. Any subsets comprising channel 4 are labelled as being detected from correctly positioned electrodes—in this case subsets 2, 3, and 4, which are labelled "C". Subsets 1, 5, and 6, which do not comprise the first bioelectrical signal, are labelled as being incorrectly placed, indicated by label "NC".

Figure 7:
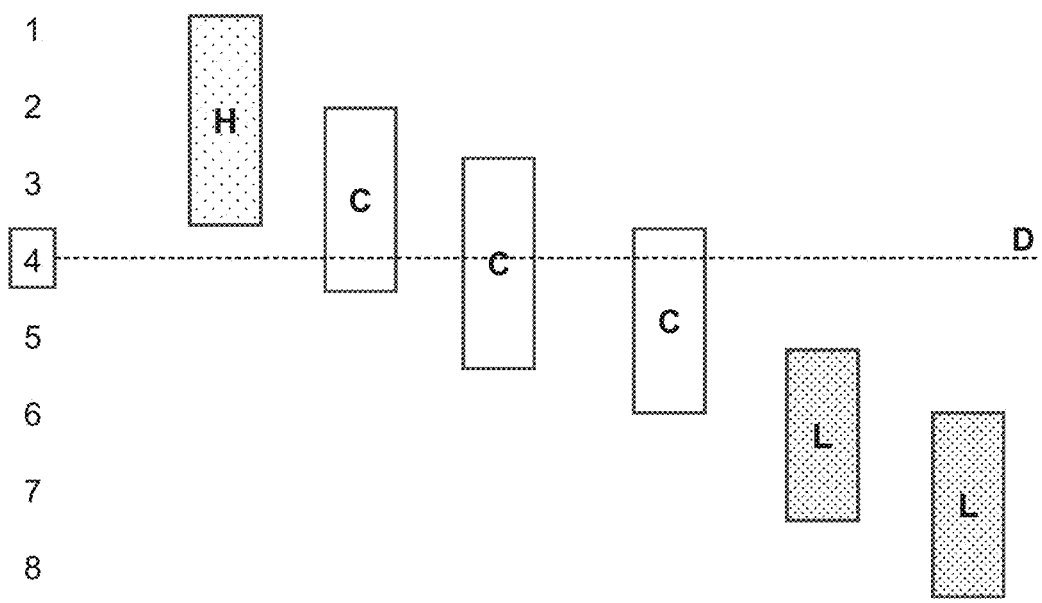

In another example of the labelling process, subsets which do not comprise the first bioelectrical signal are labelled according to whether they are associated with electrodes which are positioned below the diaphragm or above the diaphragm. FIG. 7 illustrates this schematically using the same data as seen in FIG. 6. Again, channel 4 is associated with the electrodes closest to the diaphragm, and subsets 2, 3, and 4 are identified as being correctly positioned. Subset 1, which comprises channels 1-3, is labelled "H" for being associated with electrodes which are above the diaphragm. Subsets 5 and 6, which comprise channels 5-7, and 6-8, respectively, are labelled "L" for being associated with electrodes which are below the diaphragm. The physical arrangement of the electrodes can be used to determine whether the electrodes are above the diaphragm or below the diaphragm. For example, it is known from the catheter and electrode design that electrode 1 is towards the proximal end of the catheter, relative to electrodes 4 and 5, so it is known that if electrodes 4 and 5 are correctly positioned, electrode 1 is inferred to be above the diaphragm. Similarly, electrode 9 is towards the distal end of the catheter and is inferred to be below the diaphragm. The configuration of the electrodes of the catheter is therefore, in examples, used to determine a labelling strategy, such as determining whether an electrode or pair of electrodes is above or below the diaphragm.

In some embodiments, when the first bioelectrical signal is identified as being associated with an electrode which is a distalmost or proximalmost electrode of the plurality of electrodes relative to the length of the catheter, the set of bioelectrical signals is not used as training data. In other words, using the example in FIG. 5, if the first bioelectric signal corresponds to channel 1 or 8, the entire set of signals (channel 1 to 8) may be disregarded when determining training data. Advantageously, sets of bioelectrical signals recorded from a catheter placed completely below or above the diaphragm may be disregarded, which in turn may improve the training data since no signals from a catheter positioned in such a way may represent correctly positioned electrodes. In particular if the EMG component is used to determine the first signal, typically one of channels 1 or 8 will be determined to have the largest EMG component (since it is closest to the diaphragm). However, since the entire catheter is positioned above (in the example of channel 8 having the largest EMG component) or below (in the example of channel 1 having the largest EMG component), none of these channels are really representative of a correctly positioned pair of electrodes, and consequently, such a dataset may be disregarded.

Importantly, the set of bioelectrical signals, which represented a correctly positioned catheter, has been divided into subsets of bioelectrical signals, some of which being labelled as incorrectly positioned because all electrodes associated with those subsets are outside the vicinity of the diaphragm, being either above or below it. In this way, the population of bioelectrical signals which can be considered as incorrectly positioned is increased relative to the original clinical data set. This can improve the effectiveness of the data when used to train a machine learning algorithm.

It will be appreciated that the labelling strategy can be modified depending on, for example, the physical arrangement of the electrodes such as the spacing of the electrodes, the number of electrodes and the regularity with which the electrodes are spaced, the size of the subsets, or the degree of overlap of the subsets.

In some examples, knowledge of the catheter and the physical arrangement of the electrodes can be used in the labelling process as additional labels to the labels indicating whether a position is correct or incorrect. For example, where a subset of bioelectrical signals does not comprise the first bioelectrical signal, the subset can be labelled with a distance measured between electrodes associated with the subset and the electrode pair associated with the first signal. For example, the distance may be between a geometrical midpoint of the electrode pair associated with the first signal, and a geometrical midpoint of the closest electrode pair of the subset which does not comprise the first bioelectrical signal, to thereby give an indication of how far electrodes associated with the subset which does not comprise the first bioelectrical signal is away from being correctly positioned. The geometrical midpoint can be considered to be a position along the length of the catheter midway between the respective electrodes. Other measures are possible, such as a distance of a geometrical midpoint of all of the associated electrodes from the geometrical midpoint of the correctly positioned electrode pair, or a nearest electrode of the associated electrodes to the nearest electrode of the correctly positioned electrode pair, for example.

At item S206, the subsets and their respective labels are stored as training data. Numerous processes can take place at the storage stage.

In some examples, downsampling of the bioelectrical signal data can be performed. For example, where the original sampling rate was 2 kHz, the signal can be down sampled to 400 Hz. A rate of 400 Hz has been found to be a safe upper bound, as frequencies below 400 Hz have been demonstrated to capture the critical information of the PQRST complex within the ECG signal. This reduction can decrease the size of the input data, thereby enhancing training speeds, without a decrease in, or with a tolerable decrease in, accuracy of the trained machine learning algorithm.

In some examples, a data balancing technique can be performed. Data balancing of the labelled data can help match a larger class with a smaller class. For example, after labelling has been performed, there may be more subsets of bioelectrical signals labelled with "H/placed too high" compared with "L/placed too low" or "correctly placed". Accordingly, "H/placed too high" can be reduced to match the size of either "L/placed too low" or "correctly placed", for example by drawing a random sample from the larger class. Similarly, all classes may be downsampled to match the size of the smallest class, for example. Producing a flat distribution of class populations can help improve accuracy of the trained machine learning algorithm by ensuring there are enough examples of each class, represented by the respective label, for the machine learning to effectively learn to identify.

In some examples, a data set reduction can be performed based on self-similarity of the bioelectrical signals, or by intermittently sampling the bioelectrical signals but without necessarily calculating the self-similarity of the bioelectrical signals. It has been observed that consecutive heartbeats within a same set of bioelectrical signals are frequently highly similar, whilst heartbeats which are separated temporally exhibit larger variation. For example, heartbeats at the start of a 10-minute recording typically vary more from heartbeats at the end of a 10-minute recording than consecutive preceding or succeeding heartbeats. Discarding similar consecutive heartbeats, whilst retaining temporally spaced heartbeats, can reduce the training data size without comprising accuracy, or with a tolerable loss of accuracy, for example, because the reduced training data still captures a diverse set of heartbeats. In some embodiments, auto-correlation techniques are employed to identify particularly different heartbeats within the bioelectrical signals to improve the diversity of heartbeats, for example. The reduced training data size can improve the processing speed, such as reducing the training time required before the trained machine learning algorithm is deployable.

Training Machine Learning Algorithm Using Training Data

An example of training a machine learning algorithm will now be described, corresponding to item S3, using the training data prepared at item S2. In general, the machine learning algorithm to be trained can be an algorithm suited to time-series classification problems. The general task of time-series classification problems is to predict a label for a whole times-series sequence based temporal patterns within that time-series sequence. More specifically, the position monitoring system 100 uses a machine learning algorithm which is able to output a position label such as correctly positioned, incorrectly positioned, too high, or too low, based on inputted bioelectrical signals of the catheter 30.

In examples, decision trees, k-Nearest Neighbours, and Support Vector Machines can be adapted for time-series classification problems. In other examples, the machine learning algorithm to be trained is a deep learning model such as a convolutional neural network, which can be particularly suited to time-series classification problems due to their ability to extract relevant features from raw ECG signals without the need for manual feature engineering, and to capture long-term dependencies in time series sequences. In particular, variants of convolutional neural networks such as the known RandOm Convolution Kernal Transform (ROCKET) and Minimally RandOm Convolution Kernel Transform (Mini-ROCKET) may be used. Algorithms utilising residual network architectures can also be used, for example.

In some examples, a transfer learning approach can be adopted to leverage pre-trained neural networks which have been trained on large data sets for conceptually similar tasks. For example, an existing time-series signal classifier could be retrained using the training data provided at item S2. This can reduce the overall computational expense of training the machine learning algorithm, for example.

Figure 8:
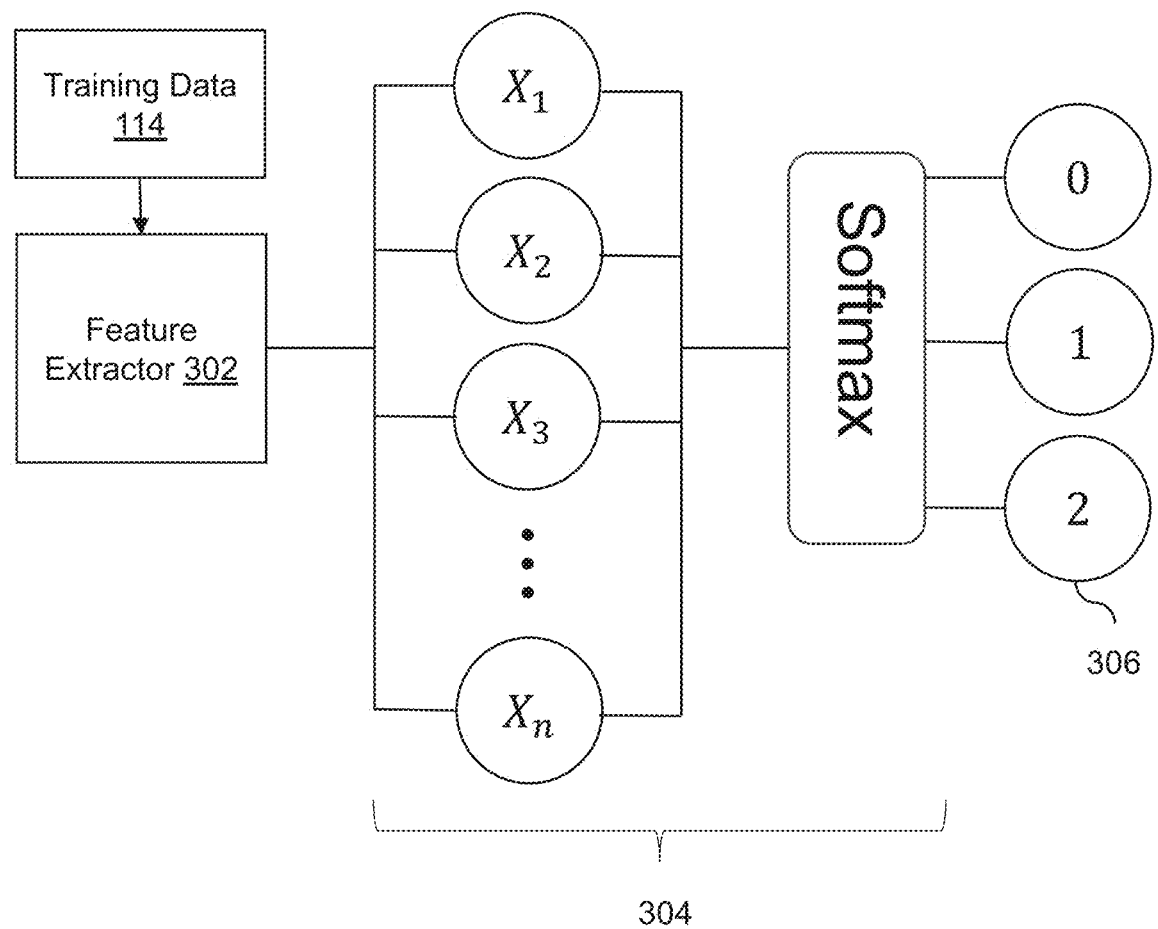
FIG. 8 illustrates an example of a machine learning architecture of the position monitoring system.

FIG. 8 illustrates schematically an architecture of a machine learning algorithm for being trained on the training data, according to an example. The architecture comprises a feature extractor 302 followed by a linear classifier 304 which outputs a classification 306.

Training can be conducted in a software environment. For example, one such software environment is Jupyter notebook.

In the example of FIG. 8, training data 114, comprising the sets of bioelectrical signals and associated labels, is initially passed into the feature extractor 302. In examples, this is a ROCKET or MiniROCKET convolutional model which employs a predetermined number of convolutional kernels to extract features. In other examples, other feature extraction models can be used.

In examples employing the ROCKET model, in a generation phase, the convolutional kernels are generated based on a random sampling of kernel attributes from predefined distributions including kernel length, weight, bias, dilation, and padding, and convolves the kernels with the training data to extract a feature for each kernel. In examples employing the MiniROCKET model, in the generation phase, random sampling of the kernel parameters is not required, and instead dilation, length, and padding parameters are fixed, and weights are constrained to two possible values, and biases are derived directly from the convolutional output.

In examples employing the ROCKET model, in a transformation phase, each generated kernel is applied to every input training data time series, yielding a corresponding feature map. Two aggregate output features are computed from the feature map: a proportion of positive values (PPV), and a maximum value, or global max pooling. The PPV metric can be considered to capture the frequency at which the time series training data exhibits a positive response to the kernel. The maximum value can be considered to capture the highest response from the time series to the respective kernel, indicating areas of maximum similarity. Accordingly, for k kernels, 2 k features are yielded. In examples employing the MiniROCKET model, in the transformation phase, the maximum value feature is not relied upon, and only the PPV value is computed.

In examples, training the feature extractor 302 can be performed using a machine learning framework such as PyTorch employing stochastic gradient descent, and in examples batch gradient descent or mini-batch gradient descent. In examples, the training can be executed using the following hyperparameter configuration:

Loss function: CrossEntropyLoss
Optimizer: Adam Algorithm
Scheduler: ReduceLROnPlateau
Batch size: 256
Learning rate: 0.0001
Patience: 5

Hyperparameter optimization can be performed through a Tree-structured Parzen Estimator (TPE), a widely recognised method for automatic hyperparameter tuning, to further optimise the training process. Execution of the TPE may allow the value of hyperparameters to be updated beyond their initially set value. For example, whilst the patience value is initially set as 5, above, following TPE this may be updated to 3, for example.

In examples, a caching-based feature extraction method can be used to allow Mini-ROCKET to perform more optimally with the size of the training data set 114. Specifically, the training data 114 can be split into several smaller chunks, and then the chunks iterated over by Mini-ROCKET to extract features which are subsequently used in the training process.

In this examples, 9996 features, corresponding to 9996 kernels, are extracted from the feature extractor 302, but it will be appreciated that the number of kernels, and hence number of extracted features, is a hyperparameter which may be different in other examples.

In the example of FIG. 8, features extracted by the feature extractor 302 are then input to a linear classifier 304 which, in this example, comprises a dense layer represented by nodes $X_1, X_2, X_3 \ldots X_n$, followed by a softmax activation function. The linear classifier can be trained on the extracted features using, for example, a Ridge or Logistic regression. The output from the softmax activation function is a label, or classification 306, of "0": Too Far Up, "1": Correct, or "2": Too Far In.

It will be appreciated that the machine learning algorithm described above is merely an example, and that other architectures are possible. The benefits of the training data prepared at item S2 described earlier are not limited to use with the specific examples of machine learning algorithms described above.

Deploying Machine Learning Algorithm

At item S4, the machine learning algorithm which has been trained at item S3 is deployed. FIG. 9 illustrates a flowchart detailing steps undertaken in deployment of and use of the deployed trained machine learning algorithm. Items S3 and S5 are included in the flowchart to help illustrate the preceding and subsequent processes to item S4.

At item S3, as described previously, a machine learning algorithm is trained using the training data prepared at item S2. More generally, however, any machine learning algorithm trained to classify each subset of bioelectrical signals into a plurality of classes, wherein one or more classes is for incorrectly positioned electrodes and at least one class is for correctly positioned electrodes, may be used with the processing for handling the outputs of the machine learning algorithm described hereafter. For example, the machine learning algorithm may have been trained on a separate, distinct system and imported to the present position monitoring system 100, and need not necessarily have been trained as per item S3.

At item S400, the trained machine learning algorithm, prepared at item S2, is deployed. Generally, this means that the machine learning algorithm is operable to receive new data, rather than training data, which comprises unseen data which does not have a known ground truth label, and for which the machine learning algorithm will generate predictions. This data can be considered live data as it will typically originate from a catheter in use on a patient. In some examples, once the training phase of item S2 has ended and the machine learning algorithm deployed, any parameters, weights, or other variables of the algorithm which are optimised during the training process are fixed. In other examples, even once deployed, further training and optimisation steps may be performed to continually improve or otherwise update the machine learning algorithm, for example. Deployment can mean that the algorithm is made available in a local computing unit such as a desktop computer from which it can be directly accessed, for example, or made available on a server such as a cloud server or a local server, for example, from which it can be remotely accessed via a network. It will be appreciated that the precise manner in which the trained machine learning algorithm is processed computationally is immaterial to the present invention, and may vary between embodiments.

At item S401, catheter data comprising bioelectrical signals detected from the patient is received. In the examples of FIGS. 1 and 2, these bioelectrical signals are detected from the catheter 30 and arrive via the catheter data input module 130. The bioelectrical signals correspond to a time period, which can vary across embodiments. For example, the bioelectrical signals may correspond to a single heart beat detected by the catheter. In other examples, the bioelectrical signals may correspond to several sequential heartbeats detected by the catheter.

Similarly to the processing of historical clinical data, described in relation to item S202, the catheter data input module 130 may perform a data preparation process to the bioelectrical signals which may comprise some form of data normalisation and/or data cleaning, for example, to ensure a degree of uniformity in the format of bioelectrical signals under consideration. In some examples, the processing may prepare the data in a way which is optimal for use with the deployed machine learning algorithm, such as preparing the data into a particular file format, for example, or removing specific components of the data which are not needed for classification purposes and otherwise disrupt the performance of the deployed machine learning algorithm. For example, the machine learning algorithm may have been trained on single heartbeats, whereas the received bioelectrical signals correspond to several sequential heartbeats. The received bioelectrical signals may be divided up into single heartbeats prior to being input to the deployed machine learning model, for example.

At item S403, the set of bioelectrical signals is divided into subsets of bioelectrical signals, wherein each subset comprises signals associated with consecutively placed electrodes. This process may be substantially similar to the process described for item S204.

At item S405, the subsets of bioelectrical signals are input to the deployed trained machine learning algorithm, and at item S407, the deployed trained machine learning algorithm generates a predicted label for each subset of bioelectrical signals. The predicted label is a form of positional information in that the machine learning algorithm, given the subsets of bioelectrical signals, prepares a prediction on whether the electrodes associated with each subset of bioelectrical signals are correctly positioned or not. As discussed previously, the positional information may be a binary classification such as "correctly positioned" or "incorrectly positioned", or may be more granular such as "too high", "correctly positioned", or "incorrectly positioned". Other predictions such as indicating a number of electrodes between the pair associated with the subset and a correctly positioned pair, or an estimated distance between the pair associated with the subset and a correctly positioned pair, may be generated instead of or in addition to the above classifications, depending on the configuration of the machine learning algorithm.

The positional information output by the machine learning algorithm and received at item S407 forms a plurality of input classifications which will be used at item S5, described further in view of FIG. 10.

Processing Machine Learning Algorithm Output to Determine Position Status

At item S5, a positioning status is determined using positional information output by the machine learning algorithm. The machine learning algorithm produces predicted classifications, which represent positional information, based on the bioelectrical signals detected by the catheter. FIG. 10 illustrates a flowchart detailing steps undertaken in determining a position status based on the positional information output by the machine learning algorithm. Items S4 and S6 are included in the flowchart to help illustrate the preceding and subsequent processes to item S5.

At item S4, as described above, the deployed machine learning algorithm is deployed, receives bioelectrical signal data detected by a catheter within a patient, and produces prediction classifications on subsets of the bioelectrical data. The output of item S4, accordingly, is a plurality of classifications which can then be used as inputs to items S501-S505 and are hereafter referred to as input classifications.

At item S501, the plurality of input classifications is input to a pattern recognition function which forms part of the position determination process 122 in FIG. 2.

At item S503, the pattern recognition function determines a positioning status of the catheter, the positioning status comprising an output classification which classifies the position of the catheter. Examples of the pattern recognition function are described in more detail shortly hereafter in view of FIGS. 11 and 12. In general, the pattern recognition function aggregates instance-level classifications, for example in the form of the input classifications, each of which corresponds to a subset of bioelectrical signals classified by the machine learning algorithm, into fewer higher level classifications, such as a single classification which classifies the overall position of the catheter. Generally, the classifications resulting from the pattern recognition process can either match the potential classes generated by the machine learning algorithm or differ from them.

At item S505, the positioning status and constituent output classification are received from the pattern recognition function, and at item S6, the positioning status is output to the user.

Examples of Pattern Recognition Functions

Figure 11:
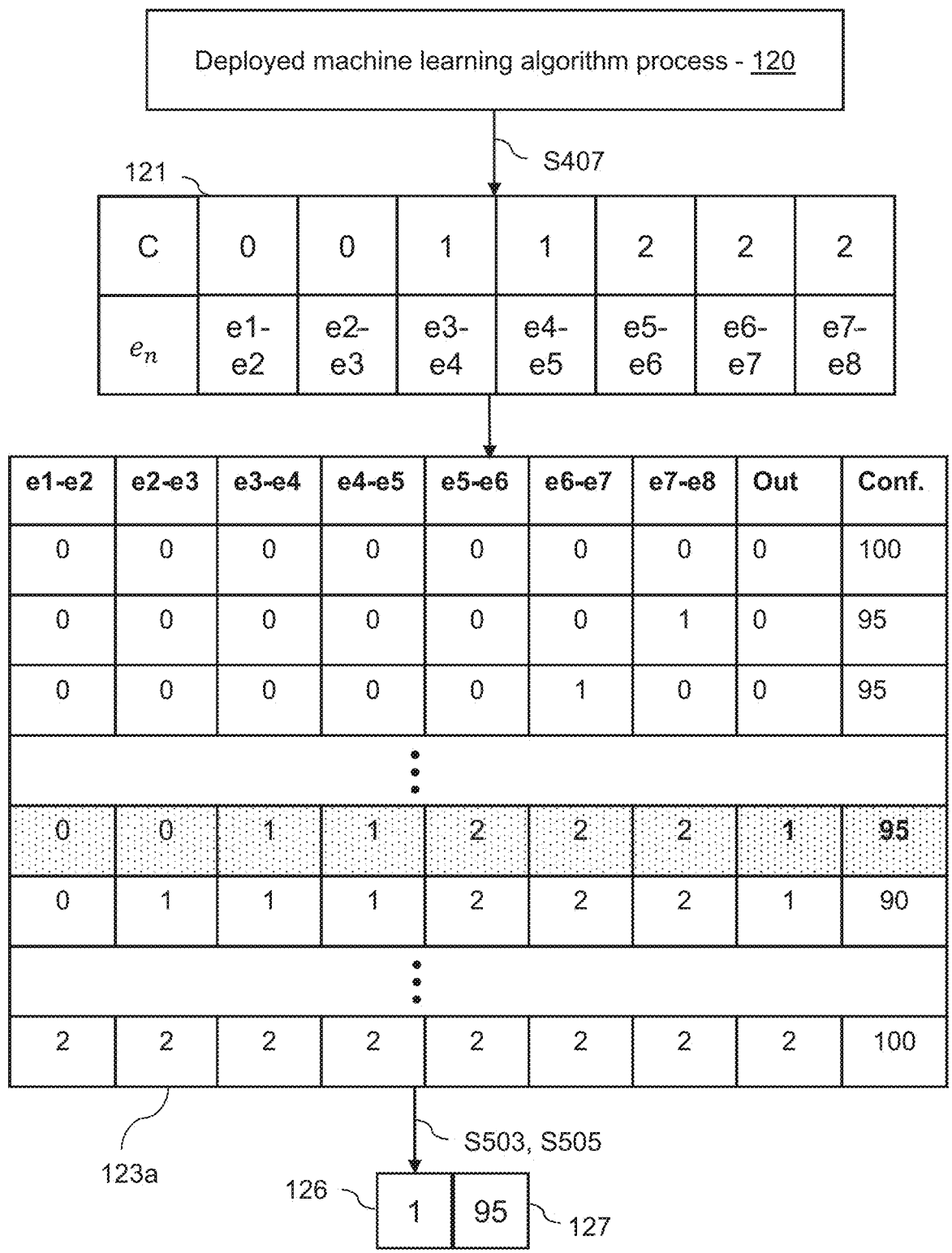
FIG. 11 is a first example of a pattern recognition function for determining a positioning status.

FIG. 11 schematically illustrates a first example of a pattern recognition function, in this example utilising a look-up table 123a to generate an output classification 126 from input classifications 121 generated by the machine learning algorithm 120.

As illustrated, in examples the input classifications 121 generated by the machine learning algorithm 120 may comprise a list of classifications "C" in association with the electrodes $e_n$ to which the classifications correspond. In this example, the input classifications 121 have classes comprising "0" which represents the associated electrodes being too high, "1" which represents the associated electrodes being correctly positioned, and "2" which represents the associated electrodes being too low. In this example, for explanatory clarity the electrodes are arranged in pairs, but as described previously other groupings are possible. In some examples, the input classifications 121 comprises a list of classifications but without the corresponding associated electrodes being explicitly stored, and the corresponding associated electrodes may be implicitly encoded in the position of the classifications. For example, it may be known that the first entry in the input classifications 121 always corresponds to electrodes e1 and e2, in which case explicitly recording the electrode identities may be unnecessary.

The look-up table 123a, in this example, lists every permutation of input classifications which are possible, hereafter referred to as candidate combinations of input classifications. For example, in the present example there are 7 classifications with 3 classes each, leading to 2187 different combinations, each of which is represented by a respective candidate combination in the look-up table 123a. Each candidate combination is stored in association with a respective candidate output classification, stored in column "Out" in the example of FIG. 11. The candidate output classification could be defined by an expert clinician, for example, or could be determined by an analysis of historical clinical data, for example. In other examples, an algorithmic approach would be employed to determine the candidate output classifications.

Given an arbitrary input classification 121, the pattern recognition function searches the look-up table 123a and finds the matching candidate combination and associated candidate output classification. The candidate output classification can then be set to the output classification 126 of the pattern recognition function.

In this example, the look-up table 123a comprises every permutation of input classifications, but in other examples may comprise a subset, such as a substantial majority of every permutation of input classifications, but nevertheless not include, for example, combinations which can be preemptively rejected because they do not give rise to a meaningful output classification. Instead, the pattern recognition function may display an "error" classification, for example, and only produce a classification related to the positioning once the input classifications match a candidate combination in the look-up table 123a. This could help diagnose a fault condition of the catheter, for example, in contrast to an incorrect positioning. It will be understood that the look-up table may comprise enough permutations of input classifications to be useable by a clinician, and edge-case combinations such as combinations which do not correspond, even allowing for inherent errors of the machine learning algorithm classification, to sensible descriptions of the catheter position, can be removed from the look-up table to save storage space, for example.

In some examples, the look-up table 123a may additionally comprise confidence values associated with each candidate combination, stored in the example of FIG. 11 in column "Conf.". The confidence value of the matching candidate combination can be output as an output confidence value 127, in association with the output classification 126. The confidence value represents a confidence that the output classification is correct, and can be considered to correspond to a probability that the output classification is correct, for example. The clinician can therefore learn how likely it is that the catheter is positioned as indicated by the output classification. In the example of FIG. 11, the confidence values range from 0 to 100, but it will be appreciated that any suitable representation is possible. The confidence value may be manually predefined by a clinician, for example, assessing the candidate combination. In other examples, the confidence value may be determined algorithmically, for example by implementing penalties for combinations which do not follow an expected pattern.

The precise contents of the look-up table 123a may vary depending on, for example, a height of the patient, a design of the catheter, and more generally factors which may impact the mapping of classifications of the constituent electrode pairings to the overall classification of the catheter position. For example, if a first design of catheter is being used on a child, a first look-up table comprising suitable candidate combinations and candidate output classifications may be used, whereas for a second design of catheter being used on an adult, a second look-up table may be used which comprises more suitable candidate combinations compared with the first look-up table. The design of the catheter may dictate, for example, the overall number of electrodes and their relative spacing, whereas the height or age of the patient may determine what constitutes a correctly positioned catheter based on the electrode signals, for example.

Figure 12:
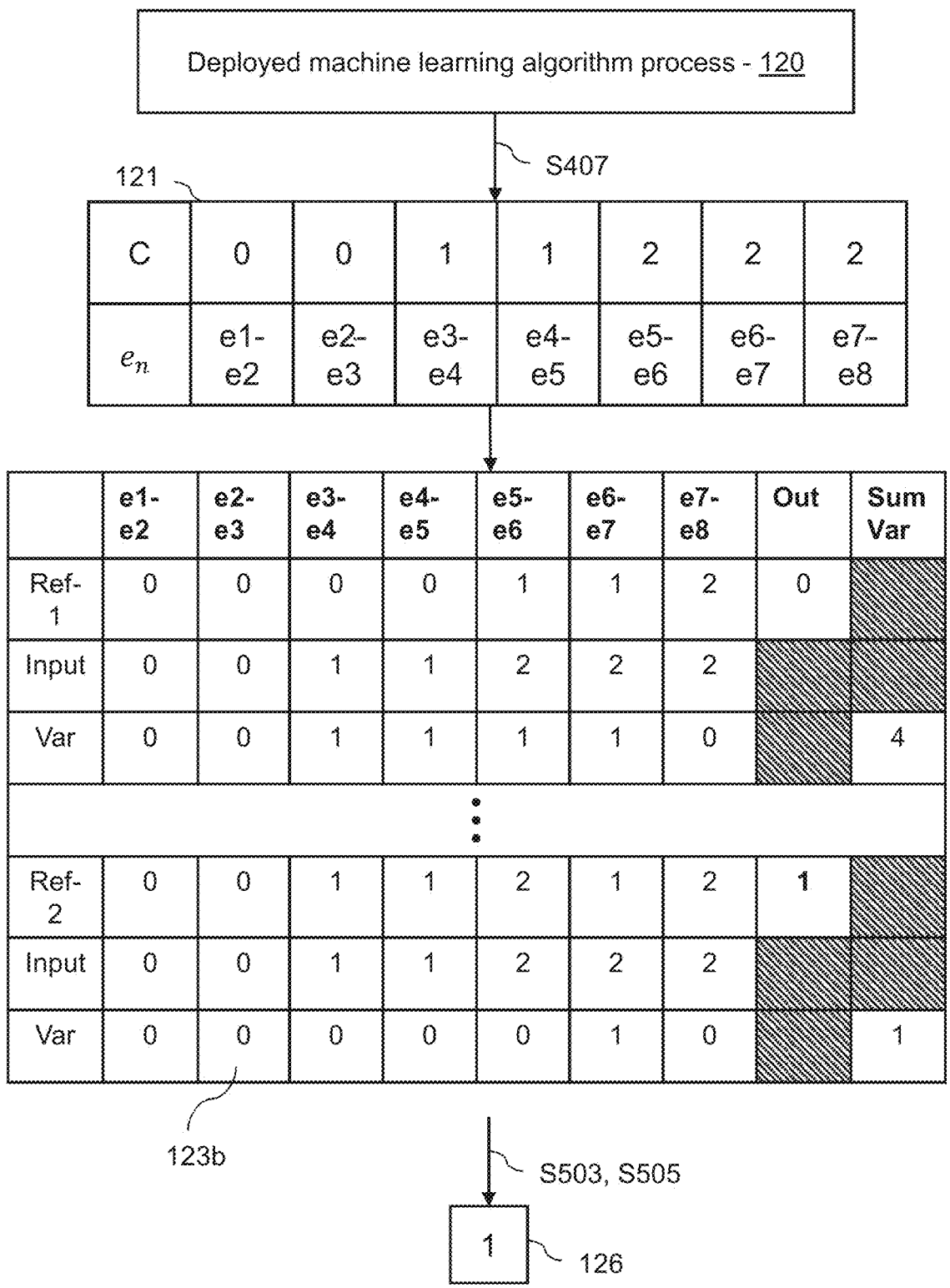
FIG. 12 is a second example of a pattern recognition function for determining a positioning status.

FIG. 12 schematically illustrates a pattern recognition function according to a second example, in this example comprising a predetermined list 123b of reference candidate combinations of classifications, similar to the look-up table of FIG. 11, but using an algorithmic approach to determine variance from the predetermined list of reference candidate combinations.

The pattern recognition function comprises a predetermined list 123b of reference candidate combinations. Each reference candidate combination is a set of reference candidate classifications, with each reference candidate classification corresponding to a subset of electrodes of a catheter, similar to the set of input classifications 121. The reference candidate combinations can thereby represent anticipated combinations of input classifications resulting from use of the catheter. The reference candidate combinations can therefore represent combinations of input classifications which arise from a correctly placed catheter, as well as input classifications which arise from a catheter being positioned too low, or too high, relative to the diaphragm, for example. Accordingly, each reference candidate combination comprises a candidate output classification based on whether it represents a catheter being correctly positioned, or positioned too low, or too high, for example.

The pattern recognition function compares a set of input classifications 121 against each reference candidate combination and calculates a variance of the input classifications from each reference candidate combination. This process can be considered to calculate how similar the input classifications are to each reference candidate combination, respectively.

In the illustrated example, this is performed by considering a difference between a reference candidate classification, stored in row "Ref-1", and the corresponding input classification 121, stored in row "Input" to calculate a channel-wise difference. The channel-wise difference between the classifications is stored in row "Var", and in this example the magnitude of the difference is taken such that the difference is stored as a positive value. The difference being channel-wise means the difference calculation is performed for each input classification and the corresponding reference candidate classification. That is, the input classification for electrodes e1-e2 is compared with a reference candidate classification for electrodes e1-e2, and the variance for e1-e2 is calculated; the input classification for electrodes e2-e3 is compared with reference classification for electrodes e2-e3, and the variance for e2-e3 calculated, and so on. This occurs for all of the reference classifications of a given reference candidate combination. The channel-wise differences are then aggregated, in this example by a summation of the variance values, and stored in the "SumVar" column, to represent a variance of the input classifications as a whole from the reference candidate combination. In other examples, a weighted aggregation may be used wherein some variance values are weighted more highly in the aggregation than others, for example. This process is repeated for a second reference candidate combination, "Ref-2", a third reference candidate combination (not shown in FIG. 12), etc.

The output classification of the pattern recognition function is then set to the candidate output classification which corresponds to the reference candidate combination with respect to which the input classifications have the lowest variance. In the example of FIG. 12, the variance of the input classifications from "Ref-1", the first reference candidate combination, is 4, and the variance of the input classifications from "Ref-2" is 1. Accordingly, the output classification of the pattern recognition function is set to the candidate output classification for "Ref-2", which is 1, corresponding to the catheter being correctly positioned.

As described above, a variance of the input classifications from reference candidate combinations can be calculated by calculating channel-wise differences in classifications and aggregating these differences. Other methods are possible. For example, only a subset of channel-wise differences may be aggregated, or even calculated in the first place. In the above examples, all electrode-pairs contribute equally to the final aggregated variance, but in some examples the position of the distalmost electrodes, e7-e9 in the example of FIG. 1, may be considered more important than the proximalmost electrodes, e1-e3 in the example of FIG. 1, in determining the overall position of the catheter, for example to reduce a risk of contacting the catheter end with the duodenum. Accordingly, a method of calculating variance may be weighted towards distalmost electrodes rather than proximalmost. In other examples, the centralmost electrodes, between the proximalmost and distalmost, may be weighted less than the proximalmost and the distalmost, as it is an observation of the inventors that it can be more difficult to classify the electrodes closest to the diaphragm, which are typically the centremost electrodes, for example.

In the above example, the variance is a simple subtraction between two classifications, but in other examples more complex functions may be used, such as a non-linear function which applies more severe penalties to larger variances compared with smaller variances. The method used can depend upon the classifications used; in the above example, there are three classifications, "0", "1" and "2", but in other examples a larger number of classifications, or a continuous quantity such as a distance measure, may be used, and therefore a different method of calculating variance may be used.

Similar to the example pattern recognition function of FIG. 11, the example pattern recognition function can output a confidence value, which in some examples can be based on the calculated variance, for example. For example, the confidence value could be calculated by an equation such as Confidence=100−(SumVar×SF), wherein SumVar is the calculated variance stored in the "SumVar" column of the predetermined list 123b of FIG. 11, and SF is a scale factor which determines the impact of the SumVar on the confidence value. For example, SF could be 10; if SumVar is always positive and does not exceed 10 then the confidence value will be a value between 0 and 100. The skilled person will appreciate that other measures of confidence value are possible, and does not necessarily need to be a positive value between 0 and 100. In other examples, some other function could be used, such as Confidence=100−SumVar$^2$, which has the effect of penalising the confidence value disproportionally more for larger aggregated variances.

In examples of the pattern recognition function, the pattern recognition function may be configured to output several classifications, each with a respective associated confidence value. For example, the pattern recognition function may output a first output classification in association with a first output confidence value, and a second output classification in association with a second output confidence value. For example, the output from the pattern recognition function might be "1: 90%; 0: 10%" which indicates that output classification "1" is 90% likely and output classification "0" is 10% likely. This approach can be readily extended to three or more output classifications, each with an accompanying confidence value, for example.

For example, in the case of the look-up table, the pattern recognition function may output the output classification associated with the candidate combination matching the input classifications, but may further consider candidate combinations within a single channel-wise change, and consider whether the output classification changes as a result of the same. For example, the pattern recognition function may check whether, if channel e4-e5 was changed from classification 1 to 0, the new matching candidate combination would have a candidate output classification different to that currently output. This could represent a scenario where the catheter is on the border between two output classifications, and both could be output with a respective corresponding confidence. The clinician can therefore get a more accurate, or more nuanced, impression of the catheter positioning.

In examples, the pattern recognition function has knowledge of previous output classifications, which can be considered memory capabilities. The pattern recognition function can be restricted, or otherwise biased towards, output classifications based on predetermined relationships between the output classifications. For example, following a "too low" classification, the pattern recognition function may be limited to, or biased towards, outputting "too low" or "correctly positioned" for a subsequent time period, rather than "too high". This can prevent erratic jumping from "too low" to "too high" which might not be otherwise expected, but may result from an erroneous classification from the machine learning algorithm, for example. The output classification is therefore smoother and can be easier to follow for a clinician, for example. The degree of restraint may be linked to the rate at which the pattern recognition function generates new output classifications and the rate at which the catheter position is anticipated to change, for example.

In the examples of FIGS. 11 and 12, the pattern recognition function outputs one of "0", "1" and "2" classifications. This corresponds to the example of classifications output by the machine learning algorithm trained at item S3. In other examples, the machine learning algorithm may output more granular classifications such as "0", "1", "2", "3", "4", and "5", corresponding to far too low, slightly too low, correctly positioned, slightly too high, much too high, for example. Alternatively, the machine learning algorithm may output a predicted distance in millimetres away from the correct position, for example, in which case the input classification may be a number between 0 and 50, for example. The pattern recognition function may nevertheless process these classifications to an output of one of "0", "1" and "2", for example. In this way, the pattern recognition function decreases the number of instance-level classes in generating an output classification. In other examples, the opposite may be true: the pattern recognition function may receive input classifications from the machine learning algorithm having classes "0", "1", and "2", and generate a more granular output classification from "0", "1", "2", "3", "4", and "5", for example.

In examples, the pattern recognition function is configured to identify anomalous behaviour. For example, if a specific subset of bioelectrical signals/pair of electrodes and hence a corresponding input classification is routinely different to the rest of the set, it can be identified and excluded from calculations of the output classification. For example, input classifications which differ from the closest matching reference candidate combination are flagged as outliers. For example, channel e2-e3 may be labelled as an outlier channel because the input classification differs from the closest reference candidate combination. If this occurs a predetermined threshold number of times in a row, for example, the channel may be flagged as faulty and ignored when determining output classifications in future. In other examples, the position system 100 more generally, or in some examples specifically the catheter data input module 130, is configured to detect noisy signals from the catheter prior to the signals being passed to the deployed machine learning algorithms, wherein the noisiness of the signal is anticipated to cause erroneous classifications by the machine learning algorithms, for example. Signal processing or catheter recalibration may be performed in such a scenario to smooth the signals to reduce noisiness, for example.

Item S5 can comprise steps to allow for time-averaging, which can render the output classification more stable and less prone to short-term switching between classifications, for example.

For example, the plurality of input classifications received from the machine learning model at item S501 may correspond to bioelectrical signals from a single heartbeat detected by the catheter. Multiple bioelectrical signals from different respective times, thereby corresponding to a plurality of heartbeats, may be gathered by the catheter data input module 130. The multiple bioelectrical signals from different respective times can be provided to the machine learning algorithm to generate a set of pluralities of input classifications, wherein each plurality of input classifications corresponds to bioelectrical signals from a respective time period. The set of pluralities of input classifications may subsequently be input to the pattern recognition function. The pattern recognition function may calculate a potential output classification for each of the pluralities of input classification, and determine an overall output classification corresponding to the majority of these potential output classifications, for example. In this way, the pattern recognition function is configured to handle input classifications corresponding to bioelectrical signals corresponding to different respective time periods.

This approach can also be adopted when the bioelectrical signals received from the catheter 30 capture multiple heartbeats, as opposed to just single heartbeats as described above. For example, a first set of bioelectrical signals received from the catheter may capture a first five heartbeats, and the machine learning algorithm may produce a first set of input classifications based on these first five heartbeats. A second set of bioelectrical signals may be received from the catheter capturing a subsequent five heartbeats and provided to the machine learning algorithm, which produces a second set of input classifications based on these subsequent second five heartbeats. The pattern recognition function may consider the first set of input classifications in conjunction with the second set of input classifications to determine an output classification, as described above. In this example, the first set of bioelectrical signals capturing the first five heartbeats corresponds to a first time period, and the second set of bioelectrical signals capturing the second five heartbeats corresponds to a second time period, the second time period subsequent to the first time period. In other examples, the time periods may partially overlap one another to allow for a moving average output classification to be calculated.

Similarly, confidence values may be based on the degree of variation between respective time periods. For example, if there is large variation between the input classifications of a first time period and a second subsequent time period, this could reduce a confidence value in the output classification. A smaller variation may increase a confidence value in the output classification, as it may indicate the behaviour or position is stable, for example.

In other examples, the input classifications undergo an averaging process prior to being passed to the pattern recognition function. For example, a straightforward numerical average could be calculated, or a majority classification for each channel could be calculated.

Monitoring Modes

In some examples, the position monitoring system 100 may disable position monitoring by the position determination process 122 whilst the catheter is in a process of being inserted by the clinician, as it can be assumed that the catheter will be incorrectly positioned during the majority of this process. The position determination process 122 may resume automatically, for example, upon detection of a trigger signal from an electrode indicating proximity to the diaphragm. The trigger signal may be a bioelectrical signal which the machine learning algorithm determines originates from a correctly positioned electrode pair with high confidence, for example. The position determination process 122 may resume manually, for example, when the clinician determines that the catheter is within a sufficiently close proximity to the diaphragm to begin the position determination process 122, for example.

In some examples, the position monitoring system 100 may be put into an approach mode and a steady state mode which affect the position determination process 122. The approach mode can reduce the time-averaging period described previously such that the user receives more frequent updates on the position. The more frequent position updates can be useful as the catheter is initially moved into position to avoid overinsertion and collision of the catheter with the patient's body, for example. Once the catheter is determined to be correctly positioned, the position monitoring system can be placed into the steady state mode which can increase time averaging, for example, to reduce short-term classification changes. In some examples, the steady-state mode includes a clinician-absent mode. This can be used in a scenario when the clinician is not actively repositioning the catheter, for example, and so any changes in position status of the catheter are assumed to result from movement of the patient, for example, or some other cause of accidental repositioning of the catheter. Accordingly, the data display output module 124 may take different actions whilst in a clinician absent mode compared with a mode in which the clinician is anticipated to be actively repositioning the catheter. For example, the position monitoring system 100 may be more sensitive to movements of the catheter or movements of the catheter above a threshold size, for example, whilst in clinician absent mode, given that movement of the catheter is not otherwise expected.

Output Positioning Status to User

Figure 13:
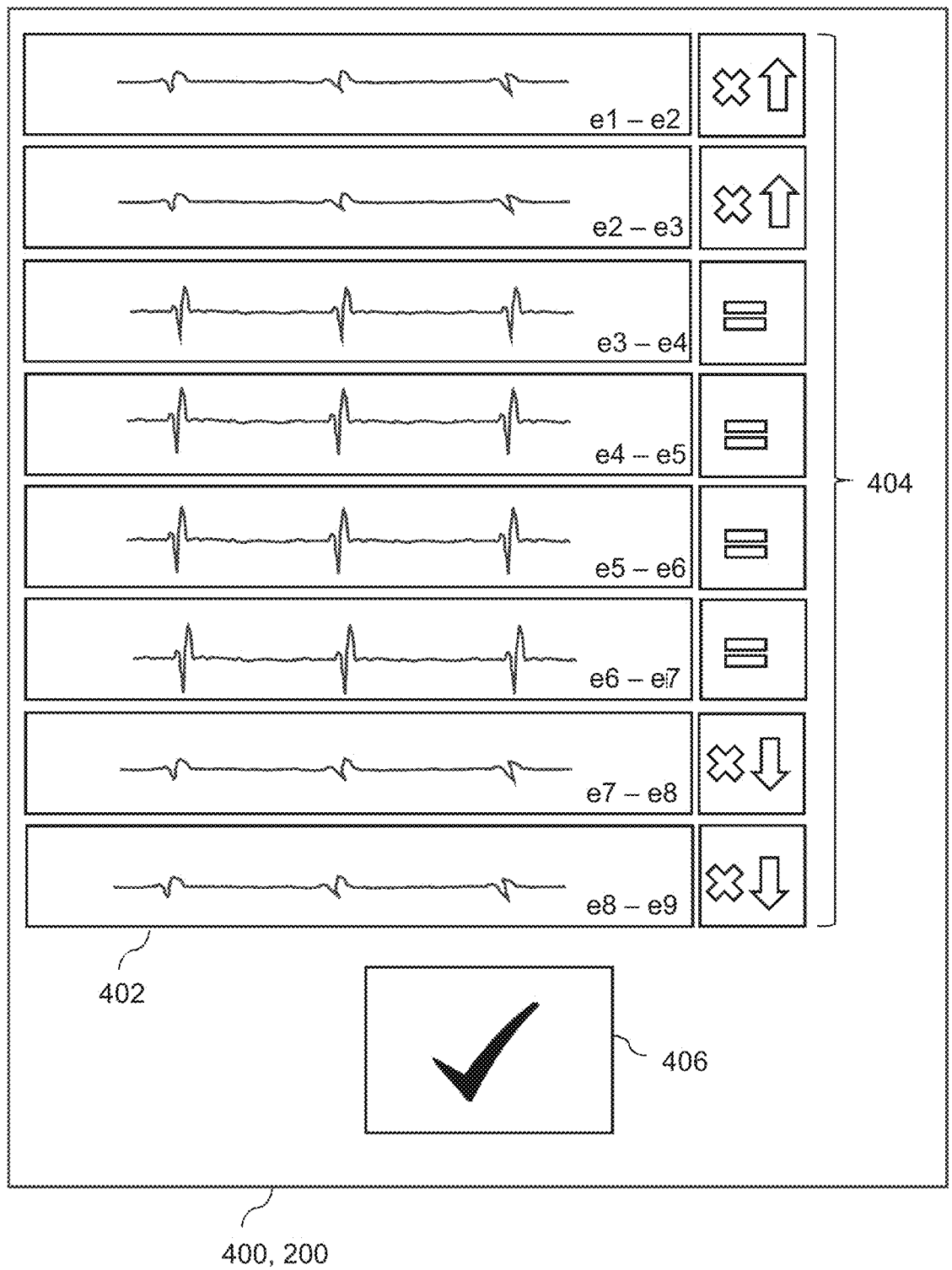
FIG. 13 schematically illustrates a display device for displaying positional information regarding the catheter to a clinician.

At item S6, the positioning status of the catheter 30 is output to the user. FIG. 13 illustrates schematically an example of a graphical user interface 400 which is displayed on display unit 200 and generally is for displaying information related to the catheter position to the clinician. The display unit 200 is controlled by the display data output module 124 which may comprise graphical processing unit and generally communicates with the processor 140 to determine information displayed by the display unit 200.

The graphical user interface 400 in this example comprises a bioelectrical signal portion 402, and a channel-wise position portion 404 and an overall catheter position portion 406 which display position status information. The bioelectrical signal portion 402 displays received bioelectrical signal data from the catheter 30 and which can be interpreted by the clinician independently from the position status information. The channel-wise position portion 404 displays classifications generated by the machine learning model, for example, thereby indicating on a channel-by-channel basis which channels and associated electrodes are correctly positioned, positioned too low, or positioned too high, for example. The overall catheter position portion 406 displays the output classification of the pattern recognition function, indicating to the clinician whether the catheter as a whole is positioned correctly, too low, or too high, for example. The information displayed by the channel-wise position portion 404 and the overall catheter position portion 406 may be achieved symbolically, for example. In other examples, text or numbers corresponding to the classification may be displayed. In examples the display may involve, additionally or alternatively, visual effects such as colours, brightness, flashing or glowing, for example, based on the output classification to improve visibility to the clinician. The bioelectrical signal portion 402 may be additionally augmented with these visual effects, for example.

In some embodiments, auditory effects may be used as well as or alternatively to the visual effects. For example, an alarm may be sounded when the position is incorrect. The alarm may further indicate in which manner the position is incorrect—for example, a first alarm sound may indicate too high, and a second alarm sound may indicate too low. Pitch or volume may vary depending on the position status, for example. The auditory effects may be managed by the display data output module 124, for example.

As described above, the display data output module may further comprise means to notify the clinician based on a position status update dependent on whether the clinician is present or not. For example, when placed in a steady-state, clinician absent mode, the display data output module may notify a clinician via an electronic communications device or increase a sound or visual effect such that the clinician can be notified whilst not actively monitoring the patient.

The display unit 200 may be an LCD, LED, OLED, CRT, or any other type of display panel capable of displaying visual content which may be part of a television or computer monitor, for example. In examples, the display unit 200 may be an augmented, mixed, or virtual reality headset worn by a clinician, for example.

FURTHER EMBODIMENTS

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method for classifying a position of a catheter in relation to a diaphragm of a patient, comprising the steps of:
   a) receiving a first set of bioelectrical signals detected by a catheter carrying a plurality of electrodes at respective positions along a length of the catheter and thereby causing the electrodes to be located at respectively different distances from a diaphragm of a patient, the plurality of electrodes being divided into a plurality of electrode pairs, each signal being detected by an electrode pair of the plurality of electrode pairs, each signal comprising an electrocardiographic, ECG, component;
   b) dividing the first set of bioelectrical signals into at least two first subsets of bioelectrical signals, each first subset of bioelectrical signals comprising one or more bioelectrical signals and corresponding to a respective group of electrodes associated with the detecting of the one or more bioelectrical signals of the subset of bioelectrical signals, wherein the dividing is performed such that each group of electrodes is a sequence of consecutively placed electrodes along the length of the catheter;
   c) inputting the first subsets of bioelectrical signals into a machine learning algorithm trained to classify each subset into a plurality of classes, the classes comprise one or more classes for incorrectly positioned electrodes and a class for correctly positioned electrodes;
   d) receiving a plurality of input classifications from the machine learning algorithm;
   e) inputting the plurality of input classifications into a pattern recognition function configured to classify the position of the catheter; and
   f) using an output classification from the pattern recognition function to classify the position of the catheter.

2. The method of claim 1, wherein the pattern recognition function is configured to output an output confidence value in association with the output classification, the output confidence value indicating a probability of correct output classification.

3. The method of claim 2, wherein the pattern recognition function is configured to output a plurality of output classifications, wherein each output classification is associated with a respective output confidence value.

4. The method of claim 1, wherein the pattern recognition function is configured to compare the plurality of input classifications with a pre-determined list comprising a plurality of candidate combinations of input classifications, wherein each candidate combination is associated with a respective candidate output classification, and wherein the method further comprises determining an output classification based on the pre-determined list.

5. The method of claim 4 wherein the method further comprises calculating a respective variance of the input classifications from each candidate combination of input classifications in the pre-determined list, and identifying the candidate combination of input classifications resulting in the smallest variance; wherein the output classification is set to the candidate output classification of the identified candidate combination.

6. The method of claim 5, wherein calculating a respective variance of the input classifications from each candidate combination comprises calculating a variance of each input classification from a respective corresponding candidate input classification of the candidate combination of input classifications, and aggregating the calculated variances to determine the respective variance of the input classifications.

7. The method of claim 5, further comprising calculating an output confidence value of the output classification based on the smallest variance.

8. The method of claim 4, wherein the pre-determined list comprises all possible permutations of input classifications as candidate combinations of input classifications, wherein the method further comprises identifying the candidate combination of input classifications from the list being identical to the input classifications, and wherein the output classification is set to the candidate output classification of the identified candidate combination.

9. The method of claim 1, wherein the first set of bioelectrical signals is the first set of a plurality of sets of bioelectrical signals, each set of the plurality of sets corresponding to bioelectrical signals detected at a respective time period; and wherein the method further comprises:
    performing step b)-d) for each set of bioelectrical signals, thus receiving a plurality of input classifications associated with each set of bioelectrical signals from the machine learning algorithm,
    forming an aggregation of input classifications which comprises the plurality of input classification received for each set of bioelectrical signals; and
    inputting the aggregation of input classifications to the pattern recognition function and receiving, as an output from the pattern recognition function, the output classification based on the aggregation of input classifications.

10. The method of claim 9, wherein the pattern recognition function calculates an intermediate output classification for each plurality of input classification of the aggregation of input classifications, and calculates the output classification based on the majority intermediate output classification.

11. The method of claim 10, further comprising calculating a respective intermediate confidence value for each intermediate output classification, and calculating an overall confidence value for the output classification based on the intermediate confidence values.

12. The method of claim 1, wherein the first set of bioelectrical signals is the first set of a plurality of sets of bioelectrical signals, each set of the plurality of sets corresponding to bioelectrical signals detected at respective time period; and wherein the method further comprises:
    performing step b)-d) for each set of bioelectrical signals, thus receiving a plurality of input classifications associated with each set of bioelectrical signals from the machine learning algorithm,
    forming an aggregation of input classifications which comprises the plurality of input classification received for each set of bioelectrical signals; and
    calculating a set of averaged input classifications based on the aggregation of input classifications; and
    inputting the set of averaged classifications to the pattern recognition function and receiving, as an output from the pattern recognition function, the output classification based on the averaged classifications.

13. The method of claim 1, wherein the pattern recognition function is configured to output one of: a first output classification corresponding to the catheter being positioned too low relative to the diaphragm of the patient, a second output classification corresponding to the diaphragm being positioned correctly relative to the diaphragm of the patient, and a third output classification corresponding to the diaphragm being positioned too high relative to the diaphragm of the patient.

14. One or more non-transitory computer-readable media storing instructions executable by one or more processors, wherein the instructions, when executed, cause the one or more processors to perform operations comprising:
    a) receiving a first set of bioelectrical signals detected by a catheter carrying a plurality of electrodes at respective positions along a length of the catheter and thereby causing the electrodes to be located at respectively different distances from a diaphragm of a patient, the plurality of electrodes being divided into a plurality of electrode pairs, each signal being detected by an electrode pair of the plurality of electrode pairs, each signal comprising an electrocardiographic, ECG, component;
    b) dividing the first set of bioelectrical signals into at least two first subsets of bioelectrical signals, each first subset of bioelectrical signals comprising one or more bioelectrical signals and corresponding to a respective group of electrodes associated with the detecting of the one or more bioelectrical signals of the subset of bioelectrical signals, wherein the dividing is performed such that each group of electrodes is a sequence of consecutively placed electrodes along the length of the catheter;
    c) inputting the first subsets of bioelectrical signals into a machine learning algorithm trained to classify each subset into a plurality of classes, the classes comprise one or more classes for incorrectly positioned electrodes and a class for correctly positioned electrodes;
    d) receiving a plurality of input classifications from the machine learning algorithm;
    e) inputting the plurality of input classifications into a pattern recognition function configured to classify the position of the catheter; and
    f) using an output classification from the pattern recognition function to classify the position of the catheter.

15. A system comprising:
one or more processors; and
one or more non-transitory computer-readable media storing first computer executable instructions that, when executed by the one or more processors, cause system to perform actions comprising:
    a) receiving a first set of bioelectrical signals detected by a catheter carrying a plurality of electrodes at respective positions along a length of the catheter and thereby causing the electrodes to be located at respectively different distances from a diaphragm of a patient, the plurality of electrodes being divided into a plurality of electrode pairs, each signal being detected by an electrode pair of the plurality of electrode pairs, each signal comprising an electrocardiographic, ECG, component;
    b) dividing the first set of bioelectrical signals into at least two first subsets of bioelectrical signals, each first subset of bioelectrical signals comprising one or more bioelectrical signals and corresponding to a respective group of electrodes associated with the detecting of the one or more bioelectrical signals of the subset of bioelectrical signals, wherein the dividing is performed such that each group of electrodes is a sequence of consecutively placed electrodes along the length of the catheter;
    c) inputting the first subsets of bioelectrical signals into a machine learning algorithm trained to classify each subset into a plurality of classes, the classes comprise one or more classes for incorrectly positioned electrodes and a class for correctly positioned electrodes;
    d) receiving a plurality of input classifications from the machine learning algorithm;

e) inputting the plurality of input classifications into a pattern recognition function configured to classify the position of the catheter; and f) using an output classification from the pattern recognition function to classify the position of the catheter.

16. The method of claim 6, further comprising calculating an output confidence value of the output classification based on the smallest variance.

17. The method of claim 8, wherein the first set of bioelectrical signals is the first set of a plurality of sets of bioelectrical signals, each set of the plurality of sets corresponding to bioelectrical signals detected at a respective time period; and wherein the method further comprises:
performing step b)-d) for each set of bioelectrical signals, thus receiving a plurality of input classifications associated with each set of bioelectrical signals from the machine learning algorithm,
forming an aggregation of input classifications which comprises the plurality of input classification received for each set of bioelectrical signals; and
inputting the aggregation of input classifications to the pattern recognition function and receiving, as an output from the pattern recognition function, the output classification based on the aggregation of input classifications.

18. The method of claim 17, wherein the pattern recognition function calculates an intermediate output classification for each plurality of input classification of the aggregation of input classifications, and calculates the output classification based on the majority intermediate output classification.

19. The method of claim 18, further comprising calculating a respective intermediate confidence value for each intermediate output classification, and calculating an overall confidence value for the output classification based on the intermediate confidence values.

20. The method of claim 9, wherein the first set of bioelectrical signals is the first set of a plurality of sets of bioelectrical signals, each set of the plurality of sets corresponding to bioelectrical signals detected at respective time period; and wherein the method further comprises:
calculating a set of averaged input classifications based on the aggregation of input classifications; and
inputting the set of averaged classifications to the pattern recognition function and receiving, as an output from the pattern recognition function, the output classification based on the averaged classifications.

* * * * *